US012767978B2

(12) United States Patent
Rodi

(10) Patent No.: US 12,767,978 B2
(45) Date of Patent: Oct. 20, 2026

(54) SYNTHETIC POLYNUCLEOTIDES AND METHODS FOR SELECTIVELY AMPLIFYING ALLELES

(71) Applicant: RHODX, Inc., St. Louis, MO (US)

(72) Inventor: Charles Rodi, St. Louis, MO (US)

(73) Assignee: RHODX, Inc., St. Louis, MO (US)

( * ) Notice: Subject to any disclaimer, the term of this patent is extended or adjusted under 35 U.S.C. 154(b) by 507 days.

(21) Appl. No.: 18/274,453

(22) PCT Filed: Feb. 2, 2022

(86) PCT No.: PCT/US2022/014908
§ 371 (c)(1),
(2) Date: Jul. 26, 2023

(87) PCT Pub. No.: WO2022/169846
PCT Pub. Date: Aug. 11, 2022

(65) Prior Publication Data

US 2024/0301481 A1 Sep. 12, 2024

Related U.S. Application Data

(60) Provisional application No. 63/144,723, filed on Feb. 2, 2021.

(51) Int. Cl.
*C12Q 1/6858* (2018.01)
*C12Q 1/6853* (2018.01)
*C12Q 1/6886* (2018.01)

(52) U.S. Cl.
CPC ......... *C12Q 1/6858* (2013.01); *C12Q 1/6853* (2013.01); *C12Q 1/6886* (2013.01)

(58) Field of Classification Search
None
See application file for complete search history.

(56) References Cited

U.S. PATENT DOCUMENTS 5,916,777 A 6/1999 Kacian et al.
2014/0038188 A1* 2/2014 Kurn .................... C12Q 1/6853 435/6.12
2017/0233791 A1* 8/2017 Spier .................... C12Q 1/6853 506/9

FOREIGN PATENT DOCUMENTS

CA 2417798 A1 * 1/2003
WO 2011085075 A2 7/2011
WO 2013123552 A1 8/2013

OTHER PUBLICATIONS

Morey et al., Microarray validation: factors influencing correlation between oligonucleotide microarrays and real-time PCR. Biol. Proced. Online 8, 175-193 (2006). doi.org/10.1251/bpo126 (Year: 2006).*

(Continued)

*Primary Examiner* — Aaron A Priest
*Assistant Examiner* — Tian Yu
(74) *Attorney, Agent, or Firm* — Gregory P. Einhorn; Greer, Burns & Crain, Ltd.

(57) ABSTRACT

In alternative embodiments, provided are primer-based nucleic acid amplification methods capable of selecting against amplification or retrieval of a particular allele while not interfering with the amplification or retrieval of any alternative alleles or mutations at a particular nucleotide position within a target sequence, or in other words, provided are methods for selectively suppressing one allele while simultaneously amplifying any alternative allele, or, provided are methods for suppressing a wild type sequence while simultaneously amplifying a point mutation, including amplifying single nucleotide variants (SNVs), insertions and deletions. In alternative embodiments, a portion of the nucleic acid composition does not selectively suppress the amplification of a specific nucleic acid target sequence, thereby providing an internal control useful in determining (Continued)

the success of the amplification and in determining relative ratios of a specific nucleic target sequence to those encoding alternative allele(s) or mutations.

21 Claims, 14 Drawing Sheets

Specification includes a Sequence Listing.

(56) References Cited

OTHER PUBLICATIONS

Cahill et al.; Exo-proofreading, a versatile SNP scoring technology. Genome Res. May 2003;13(5):925-31. doi: 10.1101/gr.939903. Epub Apr. 14, 2003. PMID: 12695330; Pmcid: PMC430895 (Year: 2003).*

RNase H-dependent PCR- Wikipedia; Archived Oct. 18, 2020 on WaybackMachine (Year: 2020).*

* cited by examiner

FIG. 1

| Position | Selector Primer with Selector Nucleotide (underlined) |
| --- | --- |
| Ultimate | AGGCCTGCTGAAAATGACTGAATATAAACTTGTGGTAGTTGGAGCTGGTGrG |
| Penultimate | GGCCTGCTGAAAATGACTGAATATAAACTTGTGGTAGTTGGAGCTGGTGrGC |
| Antepenultimate | GCCTGCTGAAAATGACTGAATATAAACTTGTGGTAGTTGGAGCTGGTGrGCG |
| Preantepenultimale | CCTGCTGAAAATGACTGAATATAAACTTGTGGTAGTTGGAGCTGGTGrGCGT |
| Propreantpenultimate | CTGCTGAAAATGACTGAATATAAACTTGTGGTAGTTGGAGCTGGTGrGCGTA |
| One before propreantepenultimate | TGCTGAAAATGACTGAATATAAACTTGTGGTAGTTGGAGCTGGTGrGCGTAG |

FIG.3

| Length | Selector Primer | D $T_M$ (WT - MUT) |
|---|---|---|
| 19 | GTAGTTGGAGCTGGTGrGCG | 4.6 |
| 25 | CTTGTGGTAGTTGGAGCTGGTGrGCG | 2.9 |
| 29 | TAAACTTGTGGTAGTTGGAGCTGGTGrGCG | 2.4 |
| 38 | GACTGAATATAAACTTGTGGTAGTTGGAGCTGGTGrGCG | 1.7 |
| 51 | GCCTGCTGAAAATGACTGAATATAAACTTGTGGTAGTTGGAGCTGGTGrGCG | 1 |
| 60 | TATTATAAGGCCTGCTGAAAATGACTGAATATAAACTTGTGGTAGTTGGAGCTGGTGrGCG | 0.9 |

FIG. 6A-B
A. Thermostable RNase H2 (IDT) cuts on the 5' side of WT rG.
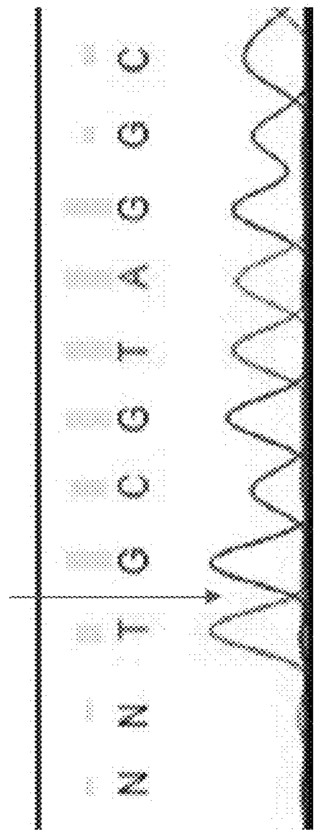
B. NaOH + heat cuts on the 3' side of WT rG.
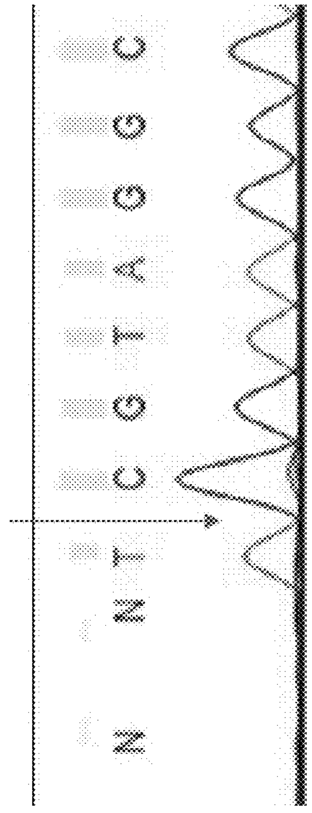

GCCTGCTGAAAATGACTGAAATATAAACTTGTGGTAGTTGGAGCTGGTGrGCG

GCCTGCTGAAAATGACTGAAATATAAACTTGTGGTAGTTGGAGCTGGTGGCG

SEQUENCE LISTING

<160> NUMBER OF SEQ ID NOS: 14

<210> SEQ ID NO 1
<211> LENGTH: 51
<212> TYPE: DNA
<213> ORGANISM: artificial sequence
<220> FEATURE:
<223> OTHER INFORMATION: synthetic oligonucleotide

<400> SEQUENCE: 1
aggcctgctg aaaatgactg aatataaact tgtggtagtt ggagctggtg g 51

<210> SEQ ID NO 2
<211> LENGTH: 51
<212> TYPE: DNA
<213> ORGANISM: artificial sequence
<220> FEATURE:
<223> OTHER INFORMATION: synthetic oligonucleotide

<400> SEQUENCE: 2
ggcctgctga aaatgactga atataaactt gtggtagttg gagctggtgg c 51

<210> SEQ ID NO 3
<211> LENGTH: 51
<212> TYPE: DNA
<213> ORGANISM: artificial sequence
<220> FEATURE:
<223> OTHER INFORMATION: synthetic oligonucleotide

<400> SEQUENCE: 3
gcctgctgaa aatgactgaa tataaacttg tggtagttgg agctggtggc g 51

<210> SEQ ID NO 4
<211> LENGTH: 51
<212> TYPE: DNA
<213> ORGANISM: artificial sequence
<220> FEATURE:
<223> OTHER INFORMATION: synthetic oligonucleotide

<400> SEQUENCE: 4
cctgctgaaa atgactgaat ataaacttgt ggtagttgga gctggtggcg t 51

<210> SEQ ID NO 5
<211> LENGTH: 51
<212> TYPE: DNA
<213> ORGANISM: artificial sequence
<220> FEATURE:
<223> OTHER INFORMATION: synthetic oligonucleotide

<400> SEQUENCE: 5
ctgctgaaaa tgactgaata taaacttgtg gtagttggag ctggtggcgt a 51

<210> SEQ ID NO 6
<211> LENGTH: 51
<212> TYPE: DNA
<213> ORGANISM: artificial sequence
<220> FEATURE:

<223> OTHER INFORMATION: synthetic oligonucleotide

<400> SEQUENCE: 6
tgctgaaaat gactgaatat aaacttgtgg tagttggagc tggtggcgta g 51

<210> SEQ ID NO 7
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 7
gcctgctgaa aatgactgaa tataaacttg tggtagttgg agctggtgrg cg 52

<210> SEQ ID NO 8
<211> LENGTH: 20
<212> TYPE: DNA
<213> ORGANISM: artificial sequence
<220> FEATURE:
<223> OTHER INFORMATION: synthetic oligonucleotide

<400> SEQUENCE: 8
gtagttggag ctggtgrgcg 20

<210> SEQ ID NO 9
<211> LENGTH: 26
<212> TYPE: DNA
<213> ORGANISM: artificial sequence
<220> FEATURE:
<223> OTHER INFORMATION: synthetic oligonucleotide

<400> SEQUENCE: 9
cttgtggtag ttggagctgg tgrgcg 26

<210> SEQ ID NO 10
<211> LENGTH: 30
<212> TYPE: DNA
<213> ORGANISM: artificial sequence
<220> FEATURE:
<223> OTHER INFORMATION: synthetic oligonucleotide

<400> SEQUENCE: 10
taaacttgtg gtagttggag ctggtgrgcg 30

<210> SEQ ID NO 11
<211> LENGTH: 39
<212> TYPE: DNA
<213> ORGANISM: artificial sequence
<220> FEATURE:
<223> OTHER INFORMATION: synthetic oligonucleotide

<400> SEQUENCE: 11
gactgaatat aaacttgtgg tagttggagc tggtgrgcg 39

<210> SEQ ID NO 12
<211> LENGTH: 52
<212> TYPE: DNA
<213> ORGANISM: artificial sequence
<220> FEATURE:
<223> OTHER INFORMATION: synthetic oligonucleotide

<400> SEQUENCE: 12
gcctgctgaa aatgactgaa tataaacttg tggtagttgg agctggtgrg cg 52

-continued

```
<210> SEQ ID NO 13
<211> LENGTH: 61
<212> TYPE: DNA
<213> ORGANISM: artificial sequence
<220> FEATURE:
<223> OTHER INFORMATION: synthetic oligonucleotide

<400> SEQUENCE: 13

tattataagg cctgctgaaa atgactgaat ataaacttgt ggtagttgga gctggtgrgc     60

g                                                                     61


<210> SEQ ID NO 14
<211> LENGTH: 60
<212> TYPE: DNA
<213> ORGANISM: artificial sequence
<220> FEATURE:
<223> OTHER INFORMATION: synthetic oligonucleotide

<400> SEQUENCE: 14

tattataagg cctgctgaaa atgactgaat ataaacttgt ggtagttgga gctggtggcg     60
```

SYNTHETIC POLYNUCLEOTIDES AND METHODS FOR SELECTIVELY AMPLIFYING ALLELES

RELATED APPLICATIONS

This application is a United States National Phase Patent application claiming benefit of priority to Patent Convention Treaty (PCT) International Application PCT/US2022/014908, filed Feb. 22, 2022, now claims the benefit of priority under 35 U.S.C. § 119 (e) of U.S. Provisional Serial Application No. (USSN) 63/144,723, filed Feb. 2, 2021. The aforementioned application applications is are expressly incorporated herein by reference in its their entirety and for all purposes. All publications, patents, patent applications cited herein are hereby expressly incorporated by reference for all purposes.

TECHNICAL FIELD

This invention generally relates to molecular biology and high-throughput sequencing such as NexGen Sequencing (NGS) of nucleic acids from, for example, genomes. In alternative embodiments, provided are primer-based nucleic acid amplification methods capable of selecting against amplification or retrieval of a particular allele while not interfering with the amplification or retrieval of any alternative alleles or mutations at a particular nucleotide position within a target sequence, or in other words, provided are methods for selectively suppressing one allele while simultaneously amplifying any alternative allele, or, provided are methods for suppressing a wild type sequence while simultaneously amplifying a point mutation, including amplifying single nucleotide variants (SNVs), insertions and deletions. In alternative embodiments, fusions in cDNAs can also be detected. In alternative embodiments, a portion of the nucleic acid composition does not selectively suppress the amplification of a specific nucleic acid target sequence, thereby providing an internal control useful in determining the success of the amplification and in determining relative ratios of a specific nucleic target sequence to those encoding alternative allele(s) or mutations. In alternative embodiments, provided are methods for diagnosing a disease or condition comprising use of a synthetic DNA polynucleotide (referred to as a selector polynucleotide) and/or a method as provided herein. In alternative embodiments, provided are methods for treating, ameliorating or preventing a disease or condition comprising use of a synthetic DNA polynucleotide (referred to as a selector polynucleotide) and/or a method as provided herein, including diagnostic methods as provided herein.

BACKGROUND

With the advent of the Liquid Biopsy, rare allele detection has become more important than ever. Circulating cell-free DNA (ccfDNA) is present in everyone's blood, and most is derived from healthy, normal cells. However, in pregnant women, small amounts of fetal DNA are also present and can be used to look for genetic diseases in a procedure known as non-invasive prenatal testing (NIPT); similarly, in solid organ transplants (SOT), minute amounts of donor-derived cell-free DNA (dd-cfDNA) can be used to detect acute rejection for a variety of organs; and in cancer, scant levels of circulating tumor DNA (ctDNA) have been used to detect early recurrence of disease. With error correction methods (e.g., molecular indexes) that improve sensitivity, specificity, and quantitation, high-throughput NexGen Sequencing (NGS) is now an excellent detection device for all of these Liquid Biopsy applications. However, the vast majority of sequence reads are uninformative: maternal reads in NIPT; recipient reads in dd-cfDNA, and wild type reads in ccfDNA. The large number of uninformative reads diminishes throughput, increases expense, and hampers detection.

Allele-specific PCR (AS-PCR) can be used to selectively amplify the desired target (a specific allele or somatic mutation), but proof-reading polymerases cannot be used, mispriming can lead to false positives, and a different primer is needed for each desired allele. Blockers against the undesired allele can also be used, but they increase the PCR assay "footprint", which with the short pieces of DNA in ccfDNA (median size of approximately 168 bp; shorter if derived from fetal or tumor DNA) lowers detection rate. Also, although it is desirable to dramatically reduce the number of uninformative reads, a set number of such reads is useful as an internal control for comparison and to ensure that the overall reaction worked. Neither AS-PCR or Blockers can do this reliably.

SUMMARY

In alternative embodiments, provided are primer-based nucleic acid compositions useful in methods that selectively suppress the amplification of a specific nucleic acid target sequence while selectively amplifying alternative allele(s) or mutation(s) present in a nucleic acid (or polynucleotide, or deoxyribonucleic acid (DNA), including cDNA) sequence that differ from the suppressed target by as little as one nucleotide, allowing for analysis and measurement of the alternative allele(s) or mutation(s). In alternative embodiments, a portion of the nucleic acid composition does not selectively suppress the amplification of a specific nucleic acid target sequence, thereby providing an internal control useful in determining the success of the amplification and in determining relative ratios of a specific nucleic target sequence to those encoding alternative allele(s) or mutations.

In alternative embodiments, provided are methods for selectively suppressing the isolation of a nucleic acid target by selectively detaching a binding moiety from a nucleic acid target. Retrieval or retention of alternative alleles or mutants of the nucleic acid target which have selectively retained a binding moiety is unaffected. In alternative embodiments, a portion of the nucleic acid composition used is not selectively detached from a binding moiety, thereby providing an internal control useful in determining the success of the retrieval and in determining relative ratios of a specific nucleic target sequence to those encoding alternative allele(s) or mutations.

In alternative embodiments, allele-specific or mutation-specific or methylation-specific amplification or capture is used to determine molecular haplotypes.

In alternative embodiments, the difference is detected by sequencing, hybridization, mass spectrometry, or any other technology that can detect sequence changes, including those with nucleotide resolution.

In alternative embodiments, provided are synthetic DNA polynucleotides (referred to as a selector polynucleotide) comprising at least a single residue (referred to as a selector nucleotide) that is located at the first (ultimate), second (penultimate), third (antepenultimate), fourth (preantepenultimate), fifth (propreantepenultimate), or sixth (one before the propreantepenultimate) position in reference to a 3' end, or is at a position that is even more distal to the 3' end, wherein the at least single residue selector nucleotide is structurally or chemically unlike any other residue within the region or section of the selector polynucleotide necessary for binding of the selector polynucleotide to a target nucleic acid, and the synthetic DNA polynucleotide (referred to as a selector polynucleotide) has a 3' end that can be: extended by a DNA polymerase, or processed to have a 3' end that can be extended by a DNA polymerase, or, the synthetic DNA polynucleotide is not blocked at its 3' end with respect to its ability to be extended by an enzyme, optionally a DNA polymerase enzyme.

In alternative embodiments of synthetic DNA polynucleotides (or selector polynucleotides) as provided herein:

the single selector nucleotide residue is located at the second position from the 3' end, or the penultimate position of the synthetic DNA polynucleotide (or selector polynucleotide);

the single selector nucleotide residue is located at the third position from the 3' end, or the antepenultimate position of the synthetic DNA polynucleotide (or selector polynucleotide);

the selector nucleotide comprises or is composed of at least one ribonucleotide, or at least one synthetic or non-natural nucleotide, and/or the selector nucleotide is a ribonucleotide.

In alternative embodiments, provided are nucleic acid amplification methods for differentiating a first nucleic acid sequence from a second nucleic acid sequence wherein the first and the second nucleic acid are in the same amplification reaction mixture, comprising:

(a) providing or having provided a synthetic DNA polynucleotide (or selector polynucleotide) as provided or described herein, wherein the synthetic DNA polynucleotide (or selector polynucleotide) contains therein a selector nucleotide residue (optionally a single ribonucleotide residue);

(b) providing or having provided a DNA polynucleotide or plurality of DNA polynucleotides, wherein optionally the DNA polynucleotide or plurality of DNA polynucleotides comprise or is derived from a genome (optionally a cell, microbial or viral genome), a cDNA library or a genomic library, and optionally the genome, cDNA library or genomic library is derived from a eukaryote or a prokaryote, a plant or a mammal (optionally a human), a microorganism (optionally a bacterium, an algae, a protist, an Archea or a fungus) or a virus or a bacteriophage;

(c) contacting, annealing or hybridizing, the synthetic DNA polynucleotide (or selector polynucleotide) to the DNA polynucleotide or plurality of DNA polynucleotides, wherein the DNA polynucleotide or plurality of DNA polynucleotides acts as a template (a template DNA polynucleotide) to the synthetic DNA polynucleotide (or selector polynucleotide) under conditions wherein the synthetic DNA polynucleotide (or selector polynucleotide) anneals or specifically hybridizes to a complementary sequence or substantially complementary sequence (for example, a sequence is a substantially complementary sequence if it has between about 95% and 99% sequence identity), in or to the DNA polynucleotide, thereby generating a nucleic acid duplex;

wherein the synthetic DNA polynucleotide (or selector polynucleotide) is either paired to the template DNA polynucleotide at the position of the selector nucleotide residue (optionally a single ribonucleotide residue) (see for example FIG. 2A, where the "R" refers to the position of a single ribonucleotide residue that is paired to the template DNA polynucleotide), or is not paired to the template DNA polynucleotide at the position of the selector nucleotide residue (optionally a single ribonucleotide residue) (see for example FIG. 2B where the "R" refers to the position of a single ribonucleotide residue that is not paired (as indicated by the "X") to the template DNA polynucleotide);

(d) contacting the duplex with a DNA polymerase enzyme having 5' to 3' extension activity and having a 3' to 5' exonuclease activity, and/or a DNA polymerase enzyme having 5' to 3' extension activity and an enzyme having 3' to 5' exonuclease activity, under conditions wherein the DNA polymerase enzyme and/or the polymerase enzyme having 5' to 3' extension activity and the enzyme having 3' to 5' exonuclease activity are enzymatically active, wherein either:

(i) the selector nucleotide residue (optionally a single ribonucleotide residue) is mismatched between the synthetic DNA polynucleotide (or selector polynucleotide) and the DNA polynucleotide or plurality of DNA polynucleotides, and the 3' to 5' exonuclease activity results in enzymatically removing portions of the synthetic DNA polynucleotide (or selector polynucleotide) from the 3' end including the selector nucleotide residue (optionally a single ribonucleotide residue) and all nucleotides 3' of the selector nucleotide prior to the DNA polymerase extending what remains of the synthetic DNA polynucleotide (or selector polynucleotide) into a new extended DNA polynucleotide that does not retain the selector nucleotide residue (optionally a single ribonucleotide residue); or (ii) the DNA polymerase extends a synthetic DNA polynucleotide (or selector polynucleotide) that is base-paired at the selector nucleotide residue (optionally a single ribonucleotide residue) with the DNA polynucleotide or plurality of DNA polynucleotides, without removing the selector nucleotide (optionally a single ribonucleotide residue), thus retaining or incorporating the selector nucleotide residue (optionally a single ribonucleotide residue) of the synthetic DNA polynucleotide (or selector polynucleotide) into a new extended DNA polynucleotide; and (e) contacting the newly created nucleic acid duplex with a ribonuclease enzyme, wherein optionally the ribonuclease enzyme is thermostable, wherein the thermostable ribonuclease is a thermostable ribonuclease H2 enzyme under conditions wherein the thermostable ribonuclease enzyme is active, wherein:

(i) if the selector nucleotide residue (optionally a single ribonucleotide residue) has been removed by the 3' to 5' exonuclease activity present in the reaction, then the portion of the synthetic DNA polynucleotide (or selector polynucleotide) that was 5' to the single selector nucleotide residue (optionally a single ribonucleotide residue) is retained within the extended synthetic polynucleotide; or (ii) if the selector nucleotide residue (optionally a single ribonucleotide residue) is retained in the extended synthetic DNA polynucleotide (or selector polynucleotide) and is matched to a deoxyribonucleotide residue, then the thermostable ribonuclease enzyme cuts at the selector nucleotide residue (optionally a single ribonucleotide residue) thereby detaching the portion of the extended synthetic DNA polynucleotide (or selector polynucleotide) that was 5' to the selector nucleotide residue (optionally a single ribonucleotide residue), wherein the extended synthetic DNA polynucleotides (or extended selector polynucleotides) that retain the portion of the synthetic DNA polynucleotide (or selector polynucleotide) that had been 5' to the selector nucleotide residue (optionally a single ribonucleotide residue) may be exponentially amplified, and wherein those extended synthetic DNA polynucleotides (extended selector polynucleotides) that have had the portion of the synthetic DNA polynucleotide (or selector polynucleotide) that was 5' to the selector nucleotide residue (optionally a single ribonucleotide residue) detached from the extended synthetic DNA polynucleotide (or selector polynucleotide) cannot be exponentially amplified and their amplification is thereby selectively suppressed, differentiating the first nucleic acid sequence from the second nucleic acid sequence.

In alternative embodiments, provided are nucleic acid amplification methods for differentiating a first nucleic acid sequence from a second nucleic acid sequence wherein the first and the second nucleic acid are in the same amplification reaction mixture, comprising:

(a) providing or having provided a synthetic DNA polynucleotide (or selector polynucleotide) as provided or described herein, wherein the synthetic DNA polynucleotide (or selector polynucleotide) contains therein a selector nucleotide residue (optionally a single selector ribonucleotide residue);

(b) providing or having provided a DNA polynucleotide or plurality of DNA polynucleotides, wherein optionally the DNA polynucleotide or plurality of DNA polynucleotides comprise or is derived from a genome (optionally a cell, microbial or viral genome), a cDNA library or a genomic library, and optionally the genome, cDNA library or genomic library is derived from a eukaryote or a prokaryote, a plant or a mammal (optionally a human), a microorganism (optionally a bacterium, an algae, a protist, an Archea or a fungus) or a virus or a bacteriophage;

(c) contacting, annealing or hybridizing, the synthetic DNA polynucleotide (or selector polynucleotide) to the DNA polynucleotide or plurality of DNA polynucleotides, wherein the DNA polynucleotide or plurality of DNA polynucleotides acts as a template (a template DNA polynucleotide) to the synthetic DNA polynucleotide (or selector polynucleotide) under conditions wherein the synthetic DNA polynucleotide (or selector polynucleotide) anneals or specifically hybridizes to a complementary sequence or substantially complementary sequence in the DNA polynucleotide, thereby generating a nucleic acid duplex;

wherein the synthetic DNA polynucleotide (or selector polynucleotide) is either paired to the template DNA polynucleotide at the position of the selector nucleotide residue (optionally a single ribonucleotide residue) (see for example FIG. 10A, where the "R" refers to the position of a single ribonucleotide residue that is paired to the template DNA polynucleotide) or is not paired to the template DNA polynucleotide at the position of the selector nucleotide residue (optionally a single ribonucleotide residue) (see for example FIG. 10B, where the "R" refers to the position of a single ribonucleotide residue that is not paired (as indicated by the "X") to the template DNA polynucleotide);

(d) contacting the nucleic acid duplex with a DNA polymerase enzyme having 5' to 3' extension activity and having a 3' to 5' exonuclease activity, and/or a DNA polymerase enzyme having 5' to 3' extension activity and an enzyme having 3' to 5' exonuclease activity, under conditions wherein the DNA polymerase enzyme and/or the polymerase enzyme having 5' to 3' extension activity and the enzyme having 3' to 5' exonuclease activity are enzymatically active, wherein either:

(i) the selector nucleotide residue (optionally a single ribonucleotide residue) is mismatched between the synthetic DNA polynucleotide (or selector polynucleotide) and the DNA polynucleotide or plurality of DNA polynucleotides, and the 3' to 5' exonuclease activity results in enzymatically removing portions of the synthetic DNA polynucleotide (or selector polynucleotide) from the 3' end including the selector nucleotide residue (optionally a single ribonucleotide residue) and all nucleotides 3' of the selector nucleotide prior to the DNA polymerase extending what remains of the synthetic DNA polynucleotide (or selector polynucleotide) into a new extended DNA polynucleotide that does not retain the selector nucleotide residue (optionally a single ribonucleotide residue); or (ii) the DNA polymerase extends a synthetic DNA polynucleotide (or selector polynucleotide) that is base-paired at the selector nucleotide residue (optionally a single ribonucleotide residue) with the DNA polynucleotide or plurality of DNA polynucleotides, without removing the selector nucleotide (optionally a single ribonucleotide residue), thus retaining or incorporating the selector nucleotide residue (optionally a single ribonucleotide residue) of the synthetic DNA polynucleotide (or selector polynucleotide) into a new extended DNA polynucleotide; and (e) after amplification the amplicons (or newly extended synthetic DNA polynucleotides or selector polynucleotides) are treated with a reagent or an enzyme that cuts on the 5' or 3' side of the selector nucleotide residue (optionally a single ribonucleotide residue), or within three nucleotides of the selector nucleotide residue (optionally a single ribonucleotide residue) when present, wherein optionally the reagent or enzyme detaches a binding moiety or a substantial amount of the incorporated synthetic DNA polynucleotide (or selector polynucleotide), or primer, from an amplicon (or newly extended DNA polynucleotide) that retained the selector nucleotide residue (optionally a single ribonucleotide residue), thus allowing amplicons, or newly extended DNA polynucleotide, that do not have the selector nucleotide residue (optionally a single ribonucleotide residue), and thus retain a binding moiety or a substantial amount of the incorporated synthetic DNA polynucleotide (or selector polynucleotide), or primer to be preferentially captured (or physically isolated) or subsequently preferentially amplified.

In alternative embodiments, methods as provided herein:

the reagent used to cut on the 5' side of the single selector ribonucleotide is a ribonuclease H2, or the reagent used to cut on the 3' side of the single selector ribonucleotide is sodium hydroxide in the presence of heat;

the methods further comprise denaturing the nucleic acid duplex to generate a single-stranded DNA, and wherein the single-stranded DNA is treated with a ribonuclease that cuts on the 3' side of the single selector ribonucleotide;

the polymerase and 3' to 5' exonuclease activities are provided by different enzymes;

synthetic DNA polynucleotide (or selector polynucleotide) is or comprises a primer used in a nucleic acid amplification method, and optionally the amplification method comprises polymerase chain reaction (PCR);

during amplification the extended synthetic DNA polynucleotide (or selector polynucleotide), or primer, is treated with an enzyme that cuts on the 5' or 3' side of the selector nucleotide residue (optionally a single ribonucleotide residue), or within three nucleotides of the selector nucleotide residue (optionally a single ribonucleotide residue), when present, thus detaching a portion of the synthetic DNA polynucleotide (or selector polynucleotide), or primer, from amplicons (or newly extended DNA polynucleotide) that retained the selector nucleotide residue (optionally a single ribonucleotide residue), and preventing the synthetic DNA polynucleotide (or selector polynucleotide), or primer, from being completely copied by extension of a return primer in the amplification reaction, and allowing amplicons that do not have the selector nucleotide residue (optionally a single ribonucleotide residue), to be preferentially amplified by virtue of retention of sufficient synthetic DNA polynucleotide (or selector polynucleotide), or primer, sequence to support exponential amplification;

the synthetic DNA polynucleotide (or selector polynucleotide), or primer, comprises a ribonucleotide and the enzyme that cuts at the 5' side of the selector nucleotide is a ribonuclease H2, and optionally the ribonuclease H2 is thermostable, and optionally the thermostable ribonuclease H2 is *Pyrococcus abysii* RNase H2;

the methods further comprise a second synthetic DNA polynucleotide or primer, that is identical to the first synthetic DNA polynucleotide (or selector polynucleotide) except that the selector nucleotide residue (optionally a single ribonucleotide residue) is replaced by a corresponding normal deoxyribonucleotide to create a DNA amplification primer, and specific amounts of this DNA amplification primer are mixed with the first synthetic DNA polynucleotide (or selector polynucleotide), or primer, containing a selector nucleotide residue (optionally a single ribonucleotide residue) in order to allow a certain amount of amplicon to be produced that would otherwise contain the selector nucleotide residue (optionally a single ribonucleotide residue), but now lacks the selector nucleotide residue (optionally a single ribonucleotide residue) and is thereby now resistant to cutting by reagents or enzymes specific to the selector nucleotide (optionally a single ribonucleotide residue);

the amplicons so produced by the second synthetic DNA polynucleotide are used as internal reaction controls to demonstrate that the amplification worked and as internal standards to which amounts of amplicons, or new extended DNA polynucleotides, produced by the first synthetic DNA polynucleotide (or selector polynucleotide) can be compared;

the sequence of the amplicon, or the new extended DNA polynucleotide, is determined by DNA sequencing, optionally using a method comprising use of Sanger sequencing, next generation sequencing (NGS), single molecule real time (SMRT) sequencing, nanopore DNA sequencing, reversible terminated chemistry (for example, SOLEXA technology (Illumina)), combinatorial probe anchor synthesis (cPAS), mass spectrometry sequencing, or massively parallel signature sequencing (MPSS);

the identity of the nucleotide corresponding to the position of an original selector nucleotide residue (optionally a single ribonucleotide residue) is determined by extension of a primer over the site of interest;

the identity and relative amounts of the nucleotides at the site of interest are determined by using or by means of a label or by mass, and optionally the identity and relative amounts of the nucleotides at the site of interest are determined by methods comprising single-base extension of a primer across the site of interest in the amplicon created using the synthetic DNA polynucleotide (or selector polynucleotide); and/or the production of amplicons of interest, or the new extended DNA polynucleotides, are determined by quantitative PCR (qPCR), digital PCR, genotyping methods, or equivalents thereof, or a combination thereof.

In alternative embodiments, provided are kits or products of manufacture comprising materials, optionally enzymes and/or synthetic DNA polynucleotides, optionally selector polynucleotides (optionally one or a plurality of synthetic DNA polynucleotides (or selector polynucleotides) as provided herein), for practicing a method as provided or described herein, and optionally further comprising instructions for practicing a method as provided or described herein.

In alternative embodiments, provided are kits comprising materials for practicing methods as provided herein, and optionally also comprising instructions for practicing methods as provided herein.

In alternative embodiments, provided are methods for diagnosing a disease or a condition comprising determining if an individual in need thereof has the disease or condition by determining the presence or absence of an allele or a genomic sequence associated with or diagnostic of the disease or condition, wherein the presence or absence of the allele or genomic sequence associated with or diagnostic of the disease or condition is determined by using a method as provided herein. The disease can be a cancer.

In alternative embodiments, provided are methods for treating, ameliorating or preventing a disease or a condition comprising treating an individual in need thereof with a drug, drug combination or treatment regimen indicated for the disease or condition, wherein the individual in need thereof is diagnosed as having, or predisposed to having, the disease or condition using a diagnostic method as provided herein. The disease can be a cancer, or the condition is an inherited disease or genetic condition.

In alternative embodiments, provided are uses of a synthetic DNA polynucleotide as provided herein for diagnosing a disease or a condition, wherein the disease or condition is diagnosed by the presence of an allele or genomic sequence associated with or diagnostic of the disease or condition, and the presence or absence of the allele or genomic sequence associated with or diagnostic of the disease or condition is determined by using a method as provided herein.

In alternative embodiments, synthetic DNA polynucleotides as provided herein are for use in diagnosing a disease or a condition, wherein the disease or condition is diagnosed by the presence of an allele or genomic sequence associated with or diagnostic of the disease or condition, and the presence or absence of the allele or genomic sequence associated with or diagnostic of the disease or condition is determined by using a method as provided herein.

In alternative embodiments, provided are methods and synthetic DNA polynucleotides for detecting the presence or absence of a rare allele in a biological specimen, comprising using a method as provided herein, wherein optionally the biological specimen comprises or is derived from a biopsy or tissue or blood sample, or liquid sample, from an individual in need thereof.

In alternative embodiments, detecting the presence or absence of the rare allele in the biological specimen is for non-invasive pre-natal testing (NIPT), or to assess tissue compatibility or detecting donor-derived nucleic acid following organ transplant (optionally solid organ or bone marrow transplant), or to assess anti-microbial resistance (AMR) or early detection of microbial resistance in the individual in need thereof, or assessing the presence of minimum residual disease (MRE), optionally assessing MRE after bone marrow ablation.

The details of one or more exemplary embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference in their entireties for all purposes.

DESCRIPTION OF DRAWINGS

The drawings set forth herein are illustrative of exemplary embodiments provided herein and are not meant to limit the scope of the invention as encompassed by the claims.

FIG. 1 illustrates possible placement of single residue ribonucleotide selector nucleotides within a selector primer; the ribonucleotide selector nucleotides are designated by an "r" placed before the nucleotide letter (in other words, the "r" is not itself a nucleotide residue, but rather is only included to clearly designate that the "G" nucleotide, which is underlined with the "r", is a ribonucleotide). The selector nucleotide may be place at the first (ultimate) (SEQ ID NO:1), second (penultimate) (SEQ ID NO: 2), third (antepenultimate) (SEQ ID NO:3), fourth (preantepenultimate) (SEQ ID NO: 4), fifth (propreantepenultimate) (SEQ ID NO:5), or sixth (one before the propreantepenultimate) (SEQ ID NO:6) position in reference to the 3' end. The ribonucleotide selector nucleotides are designated by an "r" placed before the nucleotide letter and are underlined. Not shown are positions that are even more distal to the 3' end where the selector nucleotide may be placed:

```
SEQ ID NO: 1, or ultimate
AGGCCTGCTGAAAATGACTGAATATAAACTTGTGGTAGTTGGAGCTGGTG

G

SEQ ID NO: 2, or penultimate
GGCCTGCTGAAAATGACTGAATATAAACTTGTGGTAGTTGGAGCTGGTGG

C
```

-continued

```
SEQ ID NO: 3, or antepenultimate
GCCTGCTGAAAATGACTGAATATAAACTTGTGGTAGTTGGAGCTGGTGGC

G

SEQ ID NO: 4, or preantepenultimate
CCTGCTGAAAATGACTGAATATAAACTTGTGGTAGTTGGAGCTGGTGGCG

T

SEQ ID NO: 5, or propreantepenultimate
CTGCTGAAAATGACTGAATATAAACTTGTGGTAGTTGGAGCTGGTGGCGT

A

SEQ ID NO: 6, or one before propreantepenultimate
TGCTGAAAATGACTGAATATAAACTTGTGGTAGTTGGAGCTGGTGGCGTA

G
```

Figure 2A:
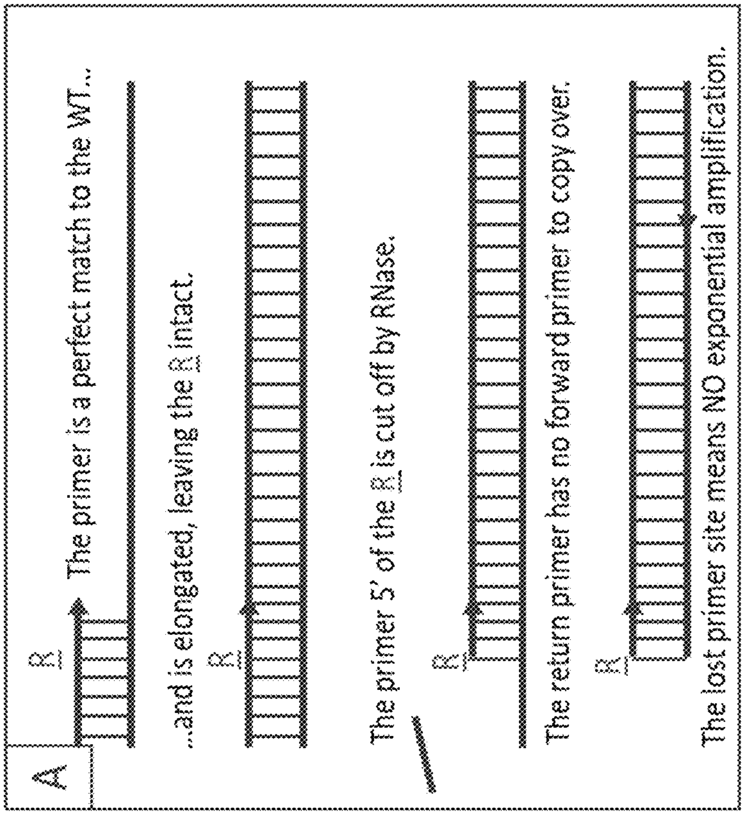
Figure 2B:
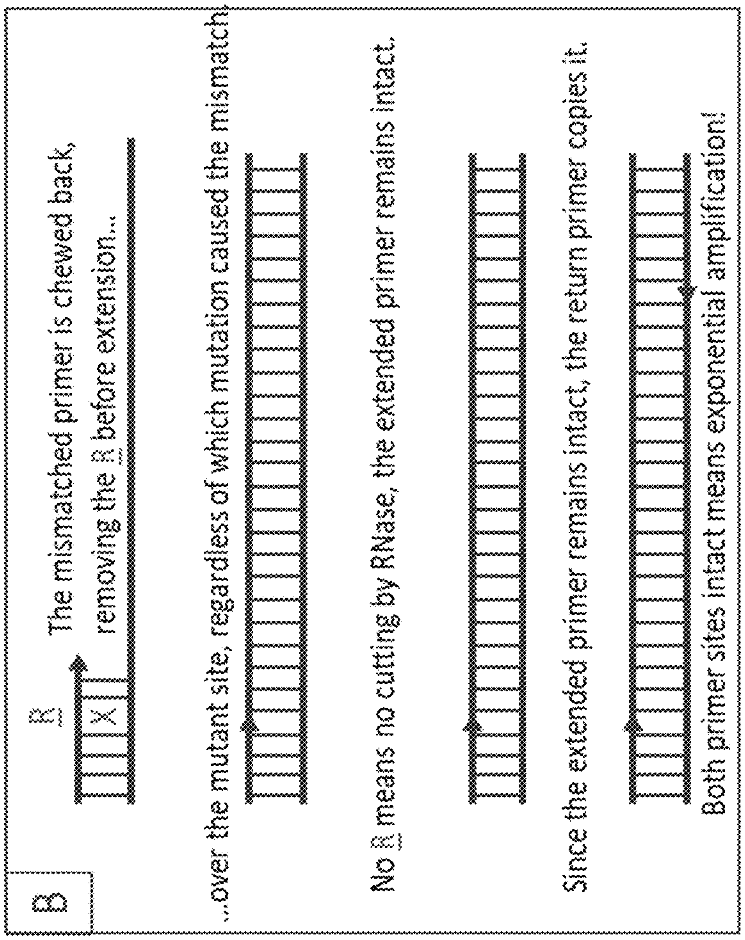

FIG. 2A-B schematically illustrate an exemplary method as provided herein for the suppression of one allele while simultaneously allowing the amplification of an alternative allele or mutation at the same nucleotide location, for example, only a mutant allele is amplified:

FIG. 2A: In the case of the allele that is to be suppressed (in this example, a wild type (WT) nucleotide), a primer, where the "R" refers to the position of a single ribonucleotide residue that is paired to the template DNA polynucleotide is an exact sequence match to the WT nucleotide of interest and is extended by a proofreading polymerase with 3' to 5' exonuclease activity. Once the primer is extended, a thermostable ribonuclease H2 (for example, a *Pyrococcus abysii* RNase H2) cuts at the 5' side of the ribonucleotide at the position marked "R" (underlined) and most of the primer sequence (at the 5' end) is removed or detached. The return primer can't copy over most of the first primer since the sequence has been removed or detached by the thermostable ribonuclease H2. This stops the allele to be suppressed (the WT allele in this example) from being exponentially amplified, greatly reducing the number of WT allelic sequences produced in the amplification reaction.

FIG. 2B: In contrast, if the single ribonucleotide in the selector primer where the "R" refers to the position of a single ribonucleotide residue that is paired to the template DNA polynucleotide is mismatched to the template (the WT allele in this example), the 3' to 5' exonuclease activity of the proofreading polymerase digests the annealed primer back through the mismatch and the single residue ribonucleotide is eliminated and when the truncated primer is extended over the mutant site, the correct deoxyribonucleotide (i.e., one matching the mutant) is used. Note that any alternative allele or any mutant at the site can be a mismatch for the wild type ribonucleotide, so for all alternative alleles or mutants the single residue mismatch ribonucleotide would be removed from the primer bound to the WT allele and replaced with the correct match for the specific mutation when the truncated primer is extended over the mutant site. The loss of the single residue ribonucleotide in the selector primer makes the incorporated (annealed) primer sequence resistant to removal by ribonuclease. A return primer can then copy over the, incorporated (i.e., partially digested, then extended) first primer, and any alternative allele or mutant sequence is exponentially amplified, greatly increasing the number of alternative allele or mutant sequences produced in the reaction should they be present. No mutant sequences are ever introduced by the selector primer. Every mutant sequence detected by subsequent analysis has passed two quality checks: first, a mutant is detected by virtue of a hybridization mismatch that results in the single residue ribonucleotide being removed; the loss of the ribonucleotide indicates that an alternative allele or mutant was present; and, second, the highly accurate polymerase copies over the alternative allele or mutant site with high fidelity (wherein optionally high fidelity means that the polymerase copies over the alternative allele or mutant site with a fidelity higher than that of TAQ polymerase), which with sequencing (or other method, such as primer extension or hybridization) reveals the identity of the alternative allele or mutant.

FIG. 3 illustrates selector primers with identical 3' ends and differing lengths of 5' ends. The selector single residue ribonucleotide is underlined and is preceded by an "r", and is positioned to be a match for the wild type nucleotide in the human gene Kirsten rat sarcoma (KRAS) at nucleotide position 38 of the coding sequence. The expected $T_M$ difference between the wild type sequence and a mutant sequence (38G>A is used here) under standard PCR conditions is noted. Increasing the length of the selector primers results in decreased differences in TMs. Decreased differences in TMS can be also achieved by using locked nucleic acids (LNAs) (also known as bridged nucleic acid (BNA), or inaccessible RNA (which is not digested by RNase H2), or a modified RNA nucleotide in which the ribose moiety is modified with an extra bridge connecting the 2' oxygen and 4' carbon), and/or other modified nucleotides, for example, modified nucleotides that increase $T_M$s in the sequence 5' to the selector nucleotide, for example, using a 2,6-diaminopurine that can base pair with dT (increases can be as much as 1-2° C. per residue); or using a 5-methyl deoxycytidine which base pairs with dG and increases $T_M$ by as much as 0.5° C. per residue.

SEQ ID NO: 7

GTAGTTGGAGCTGGTG<u>rG</u>CG

SEQ ID NO: 8

CTTGTGGTAGTTGGAGCTGGTG<u>rG</u>CG

SEQ ID NO: 9

TAAACTTGTGGTAGTTGGAGCTGGTG<u>rG</u>CG

SEQ ID NO: 10

GACTGAATATAAACTTGTGGTAGTTGGAGCTGGTG<u>rG</u>CG

SEQ ID NO: 11

GCCTGCTGAAAATGACTGAATATAAACTTGTGGTAGTTGGAGCTGGTG<u>rG</u>CG

SEQ ID NO: 12

TATTATAAGGCCTGCTGAAAATGACTGAATATAAACTTGTGGTAGTTGGAGCTGGTG<u>rG</u>CG

Figure 4:
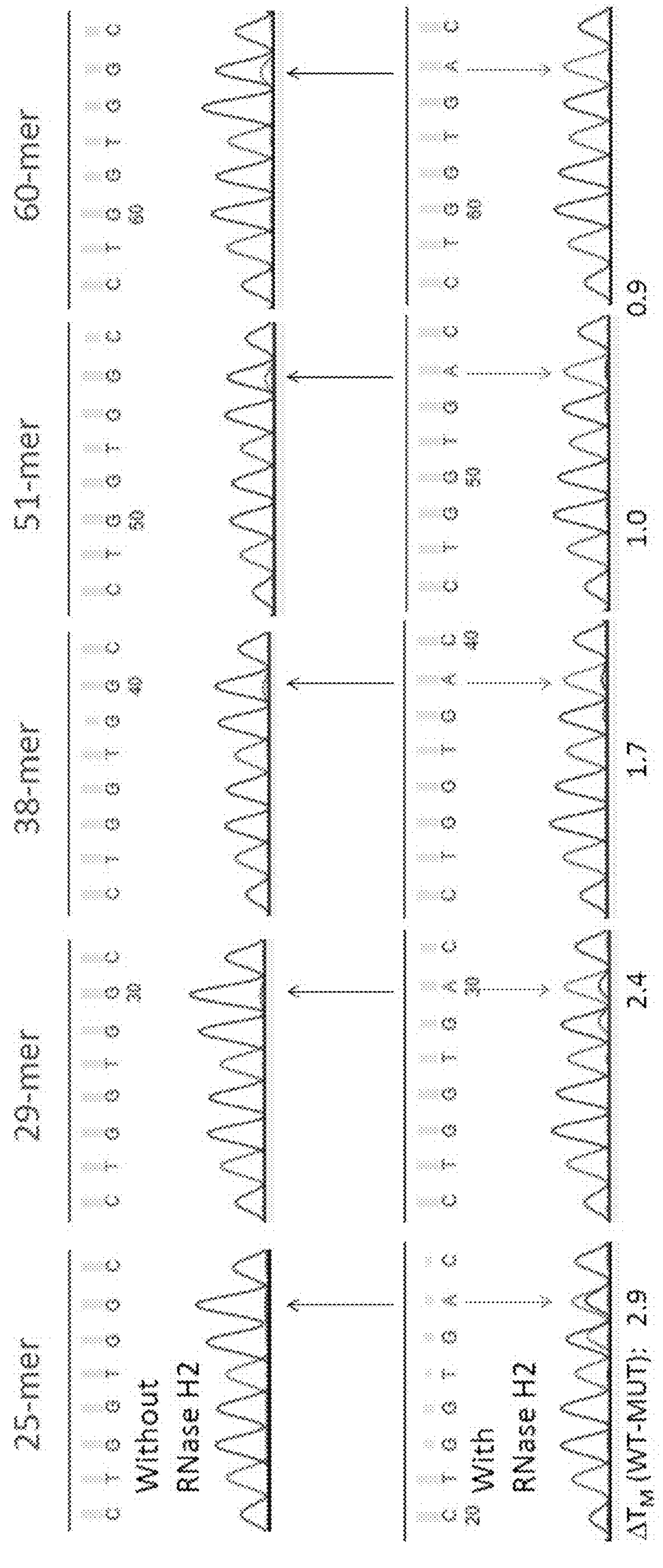

FIG. 4 illustrates Sanger sequencing traces of amplicons produced by PCRs run with each one of the primers depicted in FIG. 3 and a common return primer. For both the top row and bottom row, the arrows indicate the position of the variable nucleotide in the target sequence (the template used is DNA extracted from a cell line that is heterozygous for the wild type and the KRAS 38G>A mutant). The top row of Sanger sequencing traces shows results for each reaction when RNase H2 was not present during the PCRs. The longer, and therefore more stable the primer, the better the mutant signal (the green trace, which is also highlighted by the arrows) is seen, though even with the 60-mer primer the green mutant "A" signal is considerably less than the black wild type "G" signal. Further stabilization, e.g., by LNAs or other nucleotide modifications that increase $T_M$, would improve these results for the mutant allele. When there is no RNase H2 present, no portion (no ribonucleotide or nucleotide residue) of the primer is removed from the primer annealed to the wild type sequence and extended; exponential amplification of the wild type occurs. When thermostable RNase H2 is included in otherwise identical reactions (bottom row), the mutant signal becomes progressively more pronounced compared to the wild type signal as a function of primer stability toward the mutant template. In the case of the wild type, the presence of the RNase H2 results in most of the primer sequence (the 5' end) being detached or removed from the extended primer, compromising exponential amplification. In the case of the mutant, the single residue ribonucleotide has been removed from the primer annealed to the mutant sequence by the 3' to 5' exonuclease activity of the proofreading polymerase prior to extension; primers extended over the mutant site are thus resistant to RNase H2 and are exponentially amplified.

Figure 5:
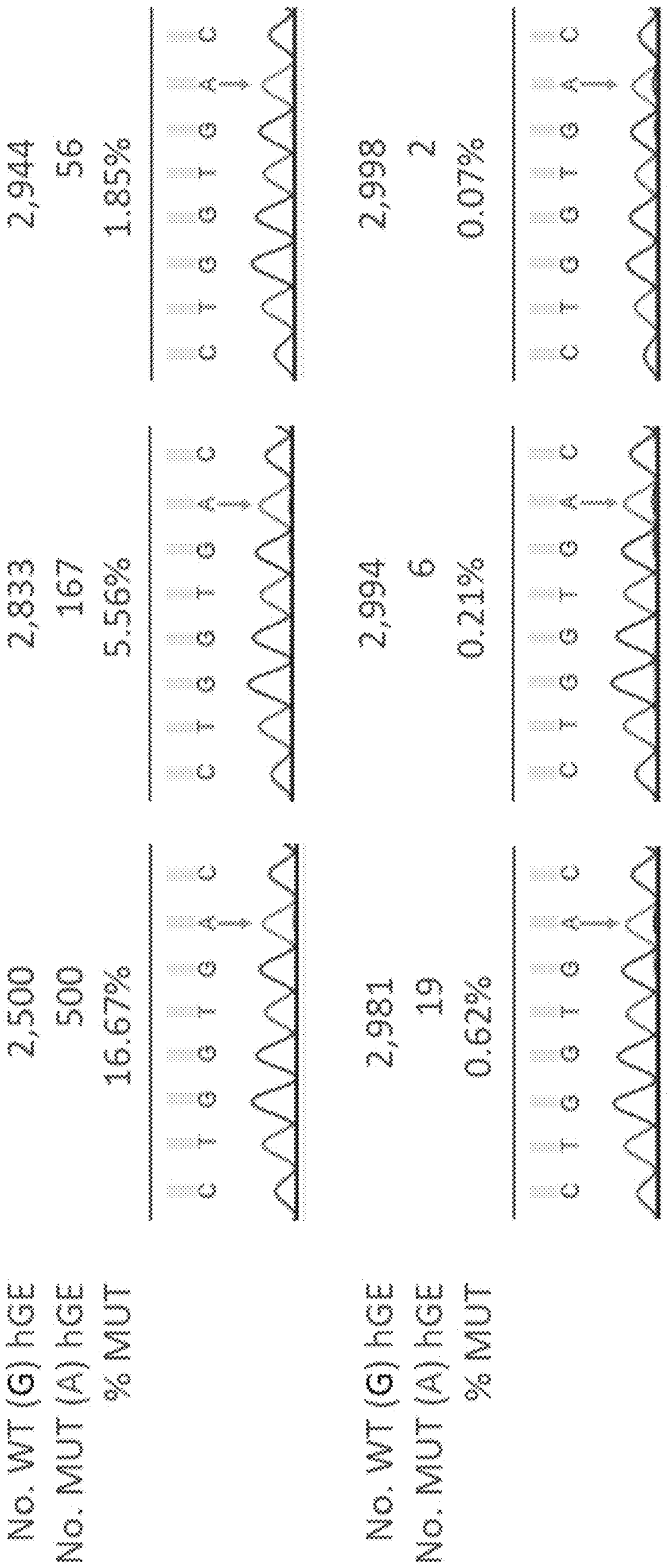

FIG. 5 illustrates Sanger sequencing results using the 51-mer selector primer depicted in FIG. 3 and a common return primer in a titration of mutant (allele A) DNA template with wild type (allele G) DNA template. The number of haploid genome equivalents calculated for both wild type (WT) and mutant (MUT) KRAS alleles is shown above each Sanger sequencing trace. Even at a calculated two copies of mutant DNA against a calculated background of 2,998 wild type DNAs, a clear mutant (A) signal is seen (bottom row, far right). At very low amounts of mutant DNA (bottom row) a very faint "G" signal can be seen; also seen are "T" signals which are not template encoded, but added by the sequencing polymerase (for example, SEQUENASE™ (ThermoFisher Scientific)), when it gets to the end of a template. That the added "T" signals are comparable in magnitude to the "G" signals indicates that primer sites have been cut from all, or virtually (or substantially) all of the WT "G" containing amplicons. Subsequent PCRs, for example, to add barcodes (such as ILLUMINA sample barcodes) will not amplify these WT sequences. Samples going forward into ILLUMINA® NGS will not bridge amplify and will not be sequenced. Because of this, any amount of mutant DNA could be detected without any or virtually (or substantially) any wild type background.

FIG. 6A-B displays results from when wild type KRAS is amplified using a selector primer in the absence of RNase H2. After amplification either: FIG. 6A, RNase H2 is added to cut on the 5' side of the ribonucleotide G (rG) and remove primer sequences upstream of the WT "G"; or: FIG. 6B, NaOH and heat are used to cut on the 3' side of the ribonucleotide G (rG) and remove primer sequences upstream of the WT "C", which is on the 3' side of the ribonucleotide G (rG). In both cases, the polymerase (SEQUENASE™) added "T" is seen, denoting the end of the processed DNA strand. Any binding moieties, for example, biotin or ILLUMINA® capture sequences, are removed from the WT-containing amplicons. Retrieval using streptavidin (for biotin) or an ILLUMINA® flow cell (for ILLUMINA® capture sequences) would capture only mutant amplicons (if present).

Figures 7, 8:
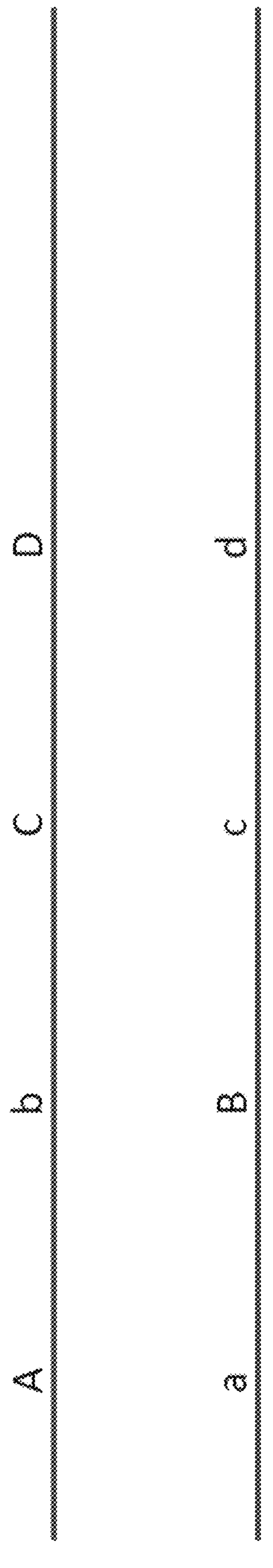

FIG. 7 depicts the 51-mer selector primer comprising the G ribonucleotide (rG) in the antepenultimate position (SEQ ID: 11) and, below it, its counterpart with a normal deoxyribonucleotide in the antepenultimate position (SEQ ID: 13). A unique feature of selector primers is that they can be fine-tuned to allow a limited number of wild type sequences.

Primers containing the G ribonucleotide (rG) can be selected against, for instance in PCR with RNase H2 present, whereas primers that lack the ribonucleotide (replaced by the deoxyribonucleotide) will be resistant to RNase H2 and can be amplified or retrieved. The value of this is that it provides an internal control that demonstrates that the specific assay worked; it also allows quantitative comparison of WT and MUT sequences between samples. The illustrated sequence is GCCTGCTGAAAATGACT-GAATATAAACTTGTGGTAGTTGGAGCTGGTGrGCG (SEQ ID NO:3), where the ribonucleotide selector nucleotide is designated by an "r" placed before the nucleotide letter (the bolded and underlined residue is the ribonucleotide). Below it in FIG. 7 is the identical sequence except the nucleotide in the antepenultimate position is a deoxyribonucleotide in place of the ribonucleotide (SEQ ID NO: 13). As shown in FIG. 3 and FIG. 4, shorter sequences can be used.

```
                                    SEQ ID NO: 13
GGCCTGCTGAAAATGACTGAATATAAACTTGTGGTAGTTGGAGCTGGTGG

CG
```

FIG. 8 illustrates the utility of methods as provided herein in performing molecular haplotyping. In this example, an individual's genotype is heterozygous at each of four sites of polymorphism. By using an appropriate selector primer, amplification of the top DNA is suppressed while amplification of the bottom DNA is unimpeded. Genotyping by a variety of means will reveal one haplotype while the other haplotype can be derived from the overall genotype, if known. If desired, in a separate reaction, the converse can be done: with the appropriate selector primer, amplification of the bottom DNA is suppressed while amplification of the top DNA is unimpeded. Genotyping of this amplicon will confirm the haplotype composition.

Figure 9:
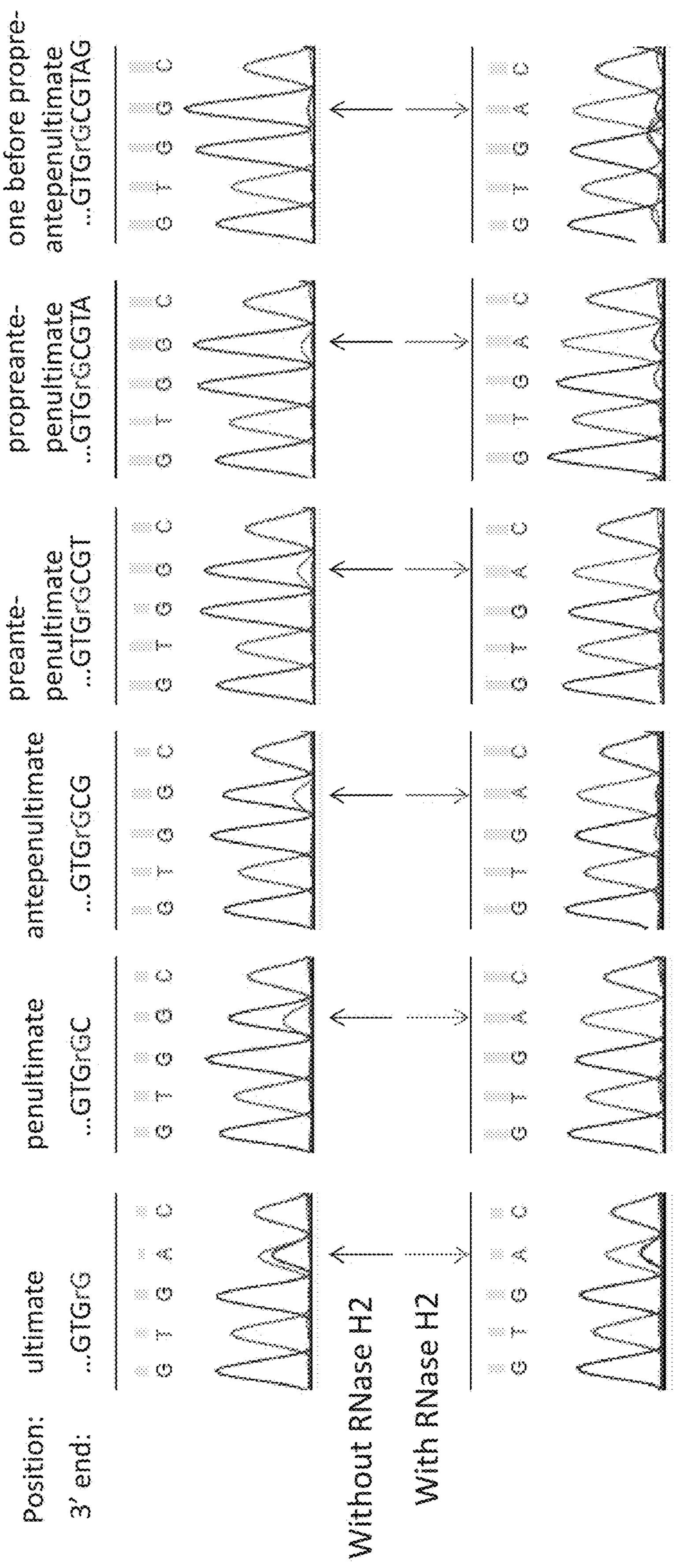

FIG. 9 illustrates Sanger sequencing results using amplicons obtained with the selector polynucleotides listed in FIG. 1; the results obtained in the absence of RNase H2 (top row) often show two traces at position 38, the wild type "G" and the mutant "A"; when the selector nucleotide is at the ultimate position in this example, the wild type "G" signal is nearly comparable to the mutant "A" signal; in all other cases, the "A" signal is of lesser magnitude than the "G" signal. In the presence of the thermostable RNase H2 (bottom row), all of the selector polynucleotides are effective in suppressing or partially suppressing the amplification of the wild type "G" containing sequence at position 38 (marked by arrows) while not interfering with the mutant "A" signal (in this case).

Figure 10A:
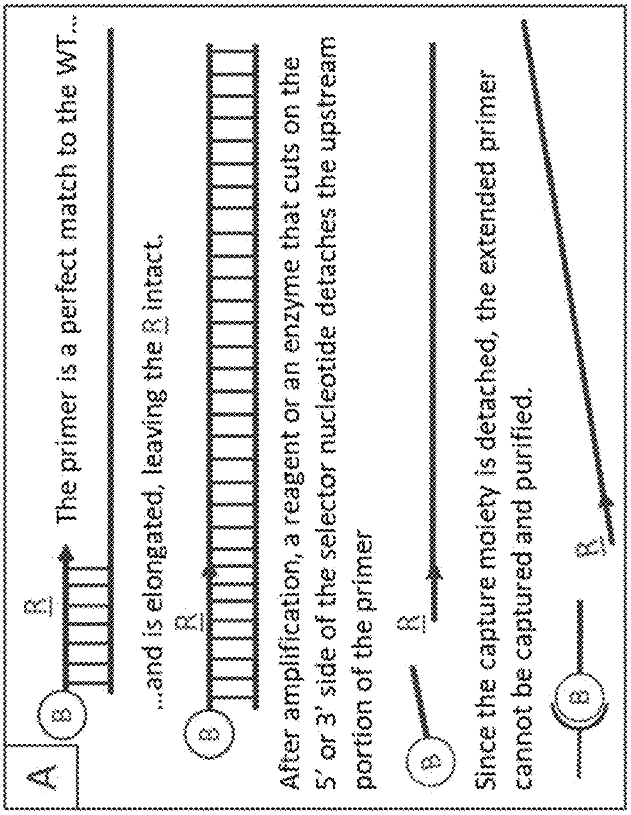
Figure 10B:
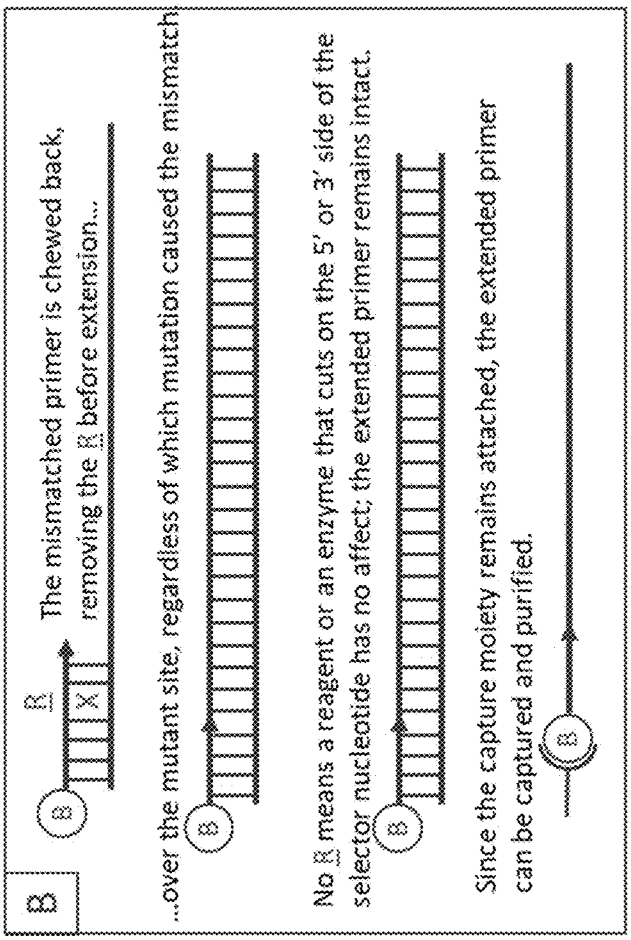

FIG. 10A-B schematically illustrate an exemplary method as provided herein where all possible alleles at the same nucleotide location are tagged with a binding moiety during amplification, but one of the alleles, for example, only a wild type allele, is detached from the binding moiety, preventing its purification:

FIG. 10A: illustrates that in the case of the allele that one does not wish to purify (in this example, a wild type (WT) nucleotide), a primer where the "R" refers to the position of a single ribonucleotide residue that is paired to the template DNA polynucleotide, for example (see also FIG. 1) that is an exact sequence match to the WT nucleotide of interest is extended by a proofreading polymerase with 3' to 5' exonuclease activity. The primer is tagged with a binding moiety, for example, a biotin, represented by a "B" within a circle in FIG. 10A; the binding moiety may also be a specific nucleotide sequence or any other moiety that would allow for its capture and purification (and subsequent detection). After amplification, the amplicons are treated with an agent or enzyme that cuts on the 5' or 3' side of the selector nucleotide (represented by an "R" and underlined in this example) which detaches the capture moiety from the extended primer that contains the wild type allele, preventing its subsequent capture and purification. In the case when the selector nucleotide is a ribonucleotide, the enzyme that cuts on the 5' side of it may be RNase H2 when the amplicon is still double-stranded; or, if denatured to a single-stranded state, ribonuclease I, which cuts on the 3' side of the ribonucleotide. Sodium hydroxide in the presence of heat can also be used to cut on the 3' side of the ribonucleotide;

FIG. 10B: illustrates, in contrast, if the single ribonucleotide in the selector primer is mismatched to the template (the WT allele in this example), the 3' to 5' exonuclease activity of the proofreading polymerase digests the annealed primer back through the mismatch and the single residue ribonucleotide is eliminated; when the truncated primer is extended over the mutant site, the correct deoxyribonucleotide (i.e., one matching the mutant) is used. Note that any alternative allele or any mutant at the site can be a mismatch for the wild type ribonucleotide, so for all alternative alleles or mutants the single residue mismatch ribonucleotide would be removed from the primer bound to the WT allele and replaced with the correct (deoxyribonucleotide) match for the specific mutation when the truncated primer is extended over the mutant site. The loss of the single residue ribonucleotide in the selector primer makes the incorporated (annealed) primer sequence resistant to removal by ribonuclease or any other treatment reliant upon the presence of the selector nucleotide. Since the capture moiety remains attached, the extended primer can be preferentially captured (or physically isolated) or subsequently preferentially amplified. No mutant sequences are ever introduced by the selector primer. Every mutant sequence detected by subsequent analysis has passed two quality checks: first, a mutant is detected by virtue of a hybridization mismatch that results in the single residue ribonucleotide being removed; the loss of the ribonucleotide indicates that an alternative allele or mutant was present; and, second, the highly accurate polymerase copies over the alternative allele or mutant site with high fidelity, which with sequencing (or other method, such as primer extension or hybridization) reveals the identity of the alternative allele or mutant.

Figure 11:
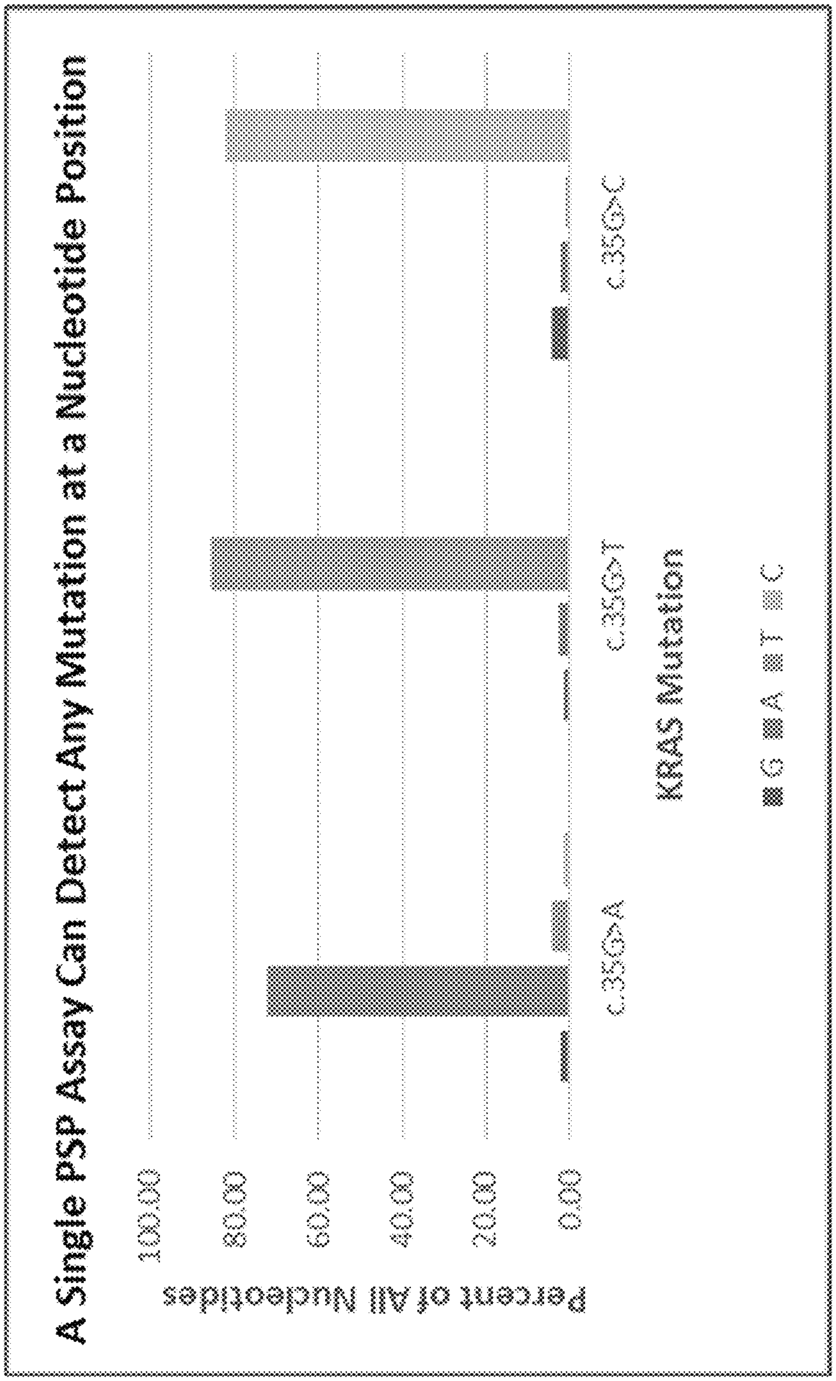

FIG. 11 graphically displays results from use of an exemplary method as provided herein that demonstrate that an exemplary single selector primer (in this case where the selector nucleotide is specific for KRAS c.35) can detect any of the three mutations that occur at that site; the exact same at master mix was applied to each of three different templates, and in each case, the KRAS c.35 selector primer detected the correct mutation, whether the KRAS c.35G>A mutant (corresponding to the G12D amino acid change); the c.35G>T mutant (G12V amino acid); or the c.35G>C mutant (the G12A amino acid), mutation was present; all three of these mutations are frequently mutated in colon cancer and seen in pancreas and lung cancers.

Figure 12:
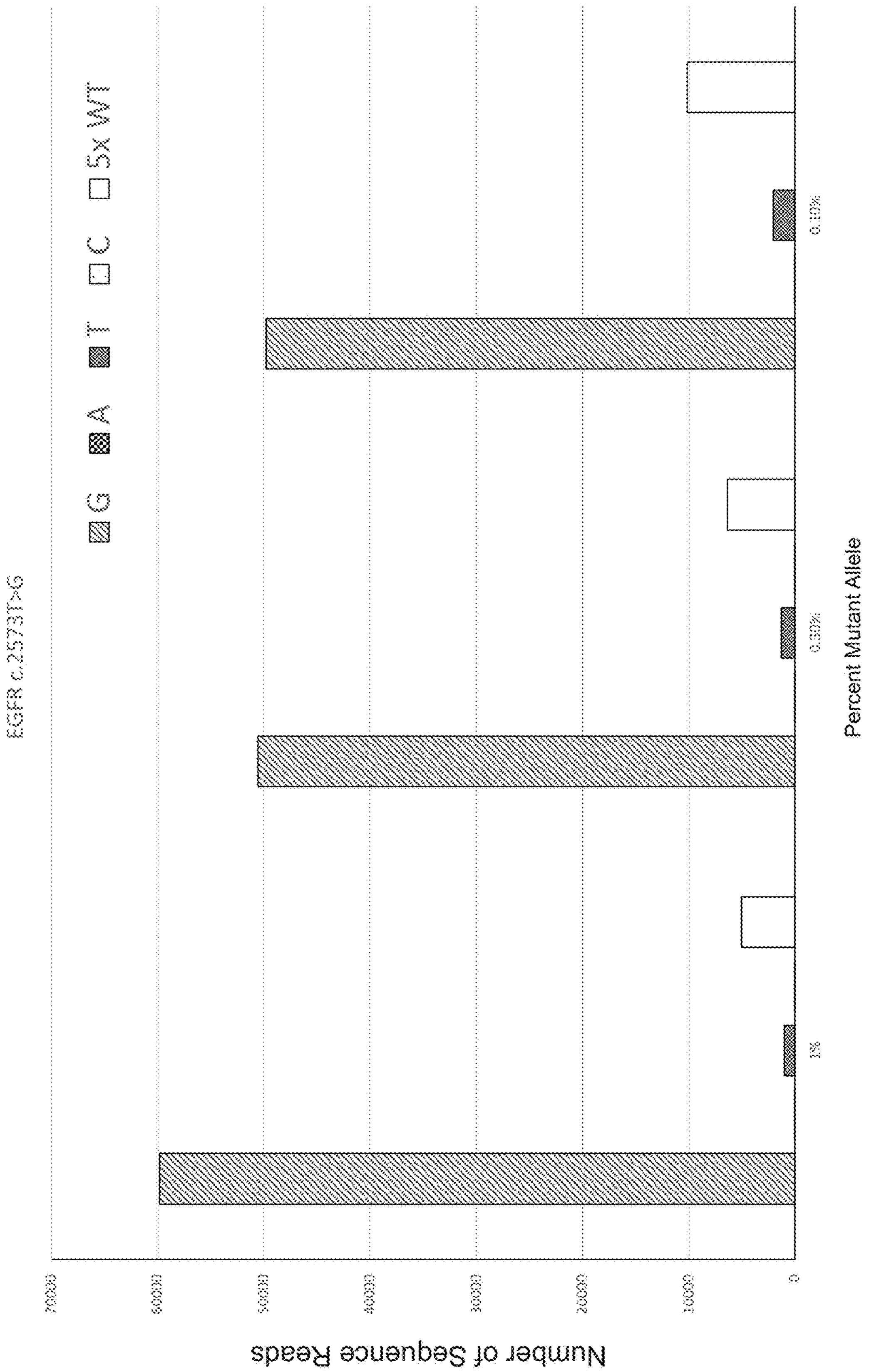

FIG. 12 graphically displays results from use of an exemplary method as provided herein that demonstrate that an exemplary selector primer (in this case where the selector nucleotide is specific for EGFR c.2573T, the T>G mutation of which results in the EGFR p.L858R mutation) can detect the mutant G allele at a frequency as low as 0.1%; the unshaded columns outlined in red are equal to five-times the wild type signal; even at 0.1% mutant allele frequency the mutation signals greatly exceed the 5× wild type values.

Figure 13:
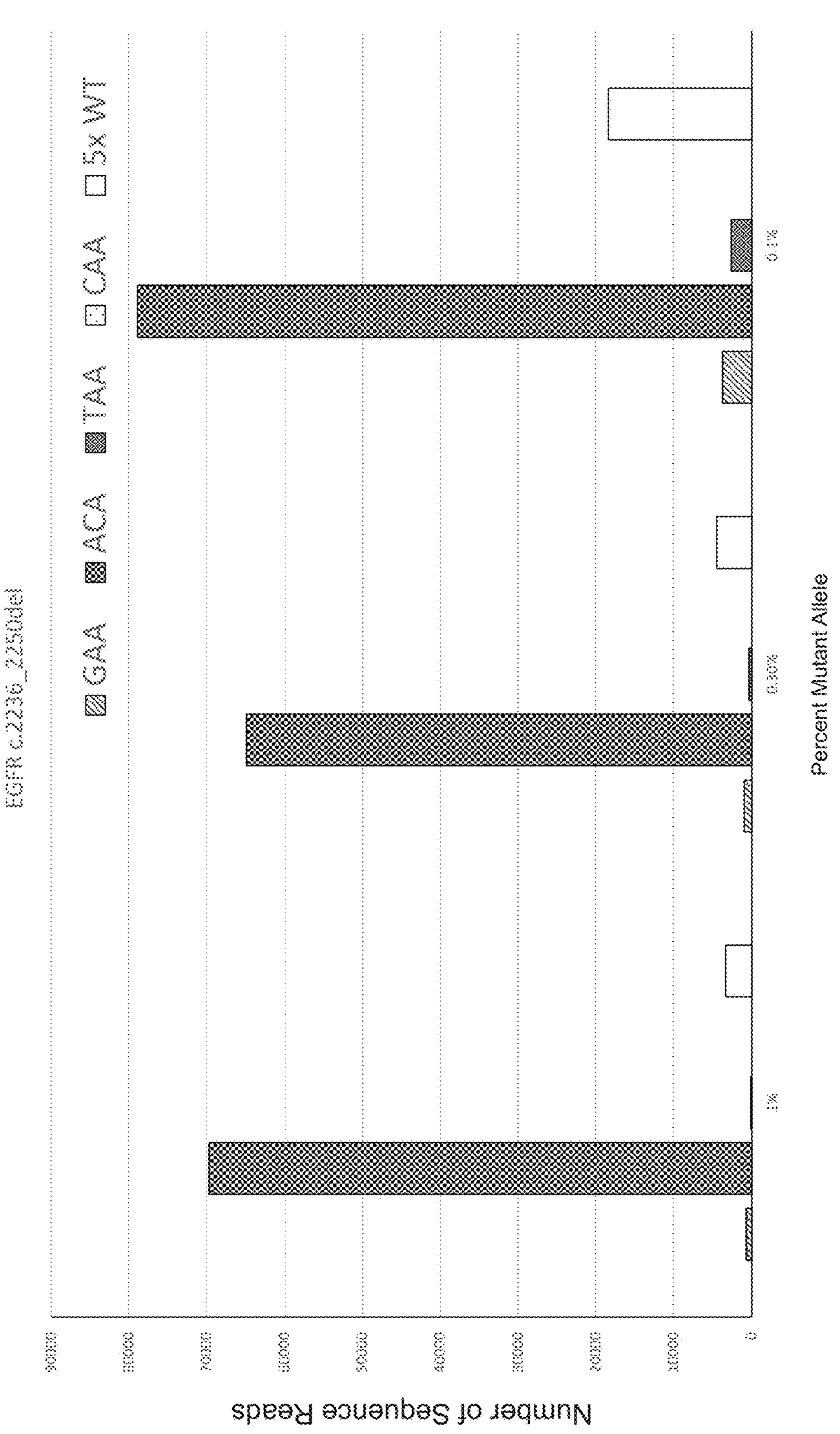

FIG. 13 displays results from use of an exemplary method as provided herein that demonstrate that an exemplary selector primer (in this case where the selector nucleotide is specific for EGFR c.2236G, the c.2236_2250 deletion mutation of which results in the EGFR p.E746_A750del mutation) can detect the mutant deletion at a frequency as low as 0.1%; the unshaded columns outlined in red are equal to five-times the wild type signal; even at 0.1% mutant allele frequency the mutation signals greatly exceed the 5× wild type values.

Figure 14:
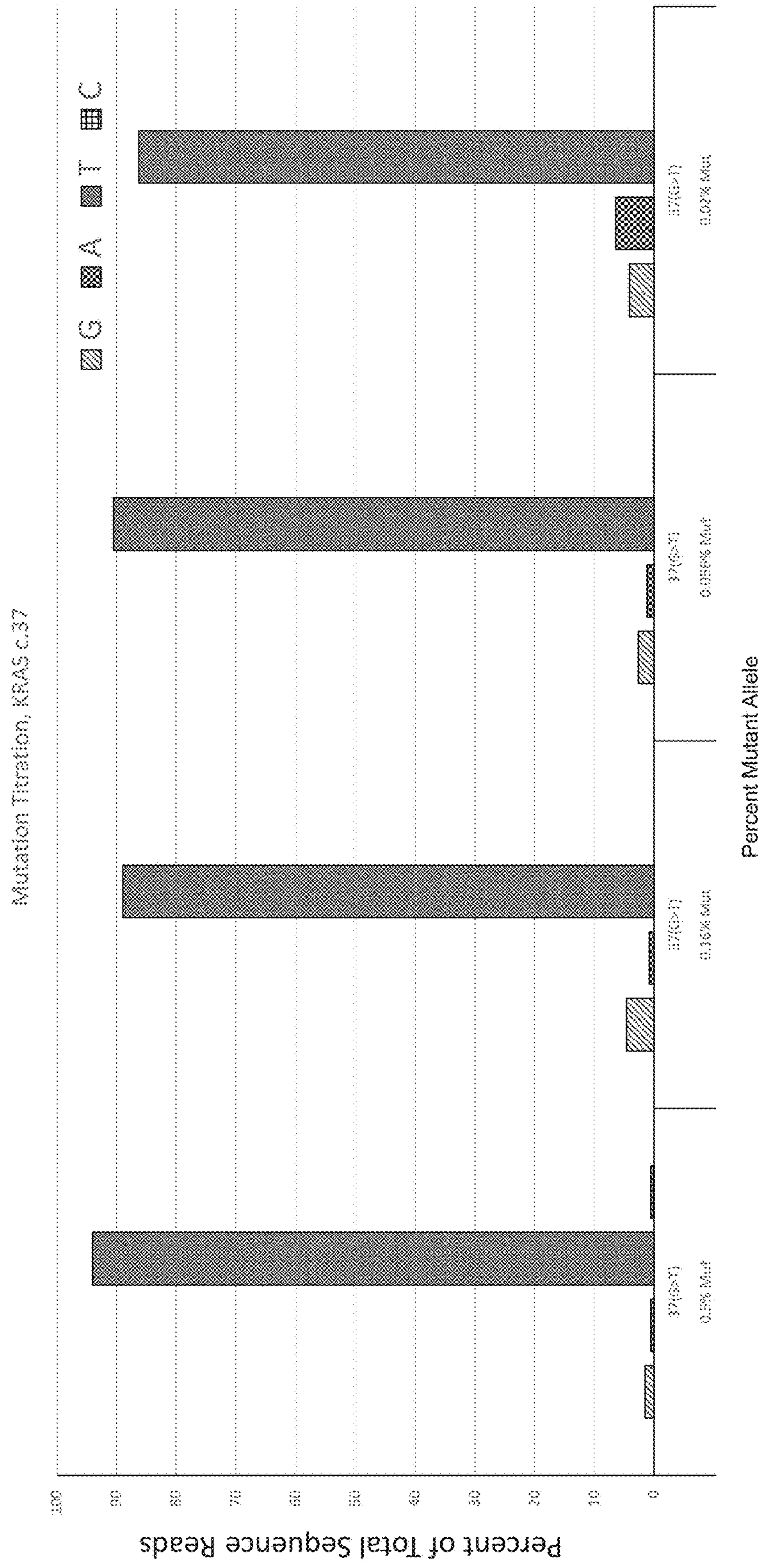

FIG. 14 displays results from use of an exemplary method as provided herein that demonstrate that an exemplary selector primer (in this case where the selector nucleotide is specific for KRAS c.37, the G>T mutation of which results in the KRAS p.G13C mutation) can detect the mutant T allele at a frequency as low as 0.02%, equivalent to finding two mutant molecules among 10,000 wild type molecules.

Figure 15:
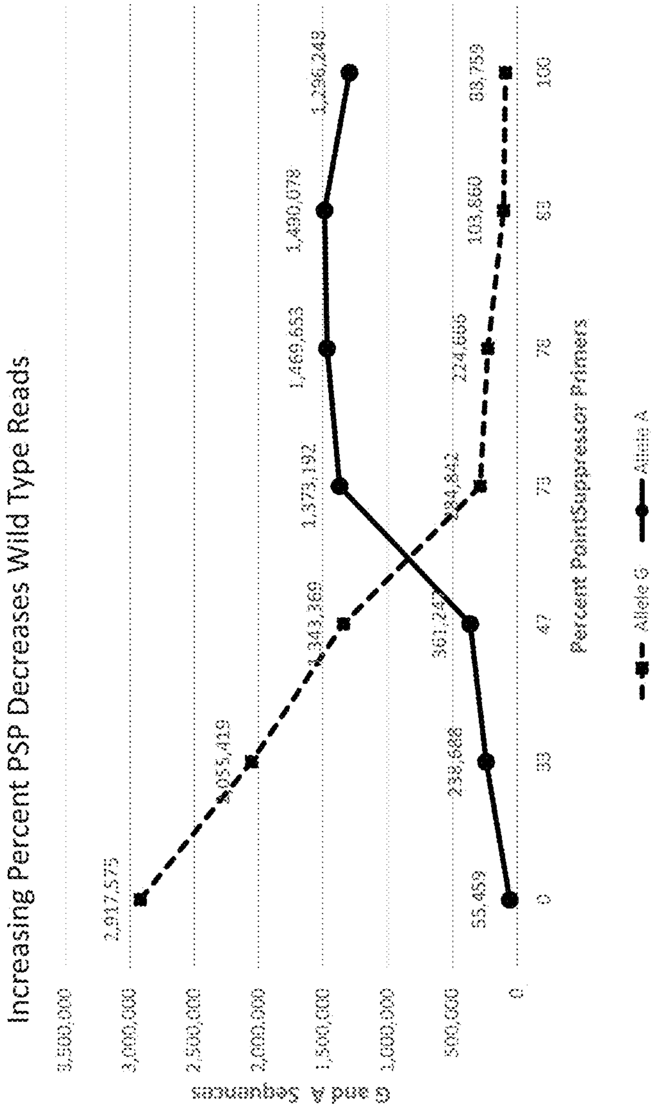

FIG. 15 displays results from use of an exemplary method as provided herein demonstrating the ability of an exemplary selector primer (in this case where the selector nucleotide is specific for KRAS c.38, the G>A mutation of which results in the KRAS p.G13D mutation) to suppress unwanted signals to a "tunable" level; a primer that is identical to the selector primer except that it contains a normal deoxyribonucleotide in place of the selector nucleotide (in this case, a ribonucleotide) is used at various mixtures with the selector primer, ranging from 0% selector primer (here referred to as PointSuppressor Primer or PSP), i.e., up to 100% selector primer; where no selector primer is used, amplification of the wild type G sequence predominates; the mutant A allele is amplified to a greater degree as the percentage of selector primer is increased.

Like reference symbols in the various drawings indicate like elements.

DETAILED DESCRIPTION

In alternative embodiments, provided are nucleic acid amplification methods which can select against a particular allele while not interfering with the amplification or retrieval of any alternative alleles or mutations at a particular nucleotide position within a target sequence, for example, a target sequence in a genome. In alternative embodiments, provided are nucleic acid amplification methods for suppressing a wild type sequence while simultaneously amplifying a point mutation, including single nucleotide variants, insertions, and deletions; and in the case of cDNA also including fusions.

In alternative embodiments, provided are methods that are "tunable", meaning that an unwanted allele can be suppressed (in an amplification or retrieval process) by a factor of 10 or 100 or by whatever amount desired. This reduces the number of uninformative reads, which increases throughput, lowers the cost per sample, and since there is reduced competition for sequencing space, enhances detection of desired targets.

In alternative embodiments, methods as provided herein have the ability to allow some uninformative reads, which is unique and allows for an internal control to demonstrate that the assay worked (as opposed to a "no result" when alternative alleles or mutants are not present in the sample) and can also function as an internal standard for quantitation.

In alternative embodiments, methods as provided herein can work with any primer-based approach, and by using a method as provided herein no variant sequences are introduced into the amplification reaction. By way of example, if one were looking for a somatic mutation, the wild type allele might be a G, and possible mutant alleles would be A, C, and T; by using an amplification method as provided herein the G-containing reads would be reduced (e.g., 100-fold) without diminishing mutant reads and any of the possible mutants would be amplified by the same single primer. The number of wild type reads is markedly reduced making mutant reads more likely to be sequenced and detected, if present, and if they are absent, the set number of wild type reads assures one that the reaction worked.

In alternative embodiments, methods as provided herein can have distinct advantages over current methods, including never introducing primers that contain the sequence that one is interested in detecting; a mutant is only detected if:

(1) The mismatch between selector primer and mutated template is recognized and removed by the 3' to 5' exonuclease activity of the proofreading polymerase, and (2) If a high-fidelity polymerase copies over the mutated template.

In contrast, allele-specific amplification introduces the variant sequence that one is interested in detecting, which can lead to false positives.

In alternative embodiments, methods as provided herein can have the advantage where a single primer detects any variant at a particular nucleotide position. In contrast, allele-specific PCR needs a specific primer for each allele variant or mutation; for example, see van Mansfeld A D, Bos J L. PCR-based approaches for detection of mutated ras genes. PCR Methods Appl. 1992 May; 1(4):211-6; Darawi, M. N., Ai-Vymn, C., Ramasamy, K. et al. Allele-specific polymerase chain reaction for the detection of Alzheimer's disease-related single nucleotide polymorphisms. *BMC Med Genet* 14, 27 (2013); Lang A H, Drexel H, Geller-Rhomberg S, et al. Optimized allele-specific real-time PCR assays for the detection of common mutations in KRAS and BRAF. *J Mol Diagn.* 2011; 13(1):23-28; Dobosy J R, Rose S D, et al. (2011) RNase H-dependent PCR (rhPCR): improved specificity and single nucleotide polymorphism detection using blocked cleavable primers. BMC Biotechnol, 11:80.

Amplification of Nucleic Acids

In alternative embodiments, provided are methods comprising use of DNA amplification techniques such as polymerase chain reaction (PCR) or other primer-based amplification method.

Any known protocol or materials (including armamentarium or enzymes) used to practice DNA amplification techniques can be used to practice methods as provided herein, including for example using a proofreading enzyme with a 5' to 3' extension activity and having a 3' to 5' exonuclease activity, and/or a DNA polymerase enzyme having 5' to 3' extension activity and an enzyme having 3' to 5' exonuclease activity. Standard materials and methods for polymerase chain reactions as used to practice methods as provided herein can be found for example: in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

An exemplary PCR protocol is shown in the following two tables, the first shows the reaction set up, the second the cycling conditions:

| Reagent | Single Reaction Volume (uL) |
|---|---|
| dH2O | 31.9 |
| 5X Phusion HF Buffer | 10.00 |
| dNTP mix (10 mM each) | 1.00 |
| DNA (37.5 ng/uL) | 0.65 |
| Selector Primer (10 uM) | 2.50 |
| Return Primer (10 uM) | 2.50 |
| RNase H2 Enzyme (IDT), diluted 1:400 | 1.00 |
| Phusion Hot Start II (ThermoFisher) | 0.50 |
| Total | 50.00 |

| Step | Temp (° C.) | Time | Cycles |
|---|---|---|---|
| Denaturation/Activation of Phusion HSII | 98 | 30 s | 1 |
| Denaturation | 98 | 10 s | |
| Annealing | 67 | 30 s | 35 |
| Extension | 72 | 30 s | |
| Final Extension | 72 | 5 min | 1 |
| Hold | 12 | Forever | |

A variety of DNA concentrations may be used, as one practiced in the art would know. Similarly, primer concentrations can vary. Any source of *Pyrococcus abyssi* RNase H2 and/or other thermostable RNase H2 enzymes can be used. Thermostable proofreading DNA polymerases from other sources may be used, including, but not limited to, Q5® HOT START HIGH-FIDELITY® DNA Polymerase from New England Biolabs, and PLATINUM SUPERFI II® DNA Polymerase-High-Fidelity PCR Enzyme from ThermoFisher.

The following are general exemplary conditions for the cycling conditions and are not intended to limit the practice of amplification: denaturation temperatures in the range of 94° C. to 98° C. with times ranging from 10 seconds to 30 seconds; annealing temperatures in the range of 55° C. to 72° C. for 5 seconds to 30 seconds; extension temperatures in the range of 55° C. to 72° C. or higher for 15 seconds to 30 seconds per kilobase of DNA to be amplified. A general discussion of PCR methodologies that can be used to practice methods as provided herein can be found for example on Wikipedia Valones M A, Guimarães R L, Brandão L A, de Souza P R, de Albuquerque Tavares Carvalho A, Crovela S. Principles and applications of polymerase chain reaction in medical diagnostic fields: a review. *Braz J Microbiol.* 2009; 40(1):1-11; Garibyan L, Avashia N. Polymerase chain reaction. *J Invest Dermatol.* 2013; 133 (3):1-4; Dieffenbach C W, Lowe T M, Dveksler G S. General concepts for PCR primer design. PCR Methods Appl. 1993 December; 3(3):S30-7). Exemplary conditions for use of RNase H2 enzyme are included in Dobosy J R, Rose S D, et al. (2011) RNase H-dependent PCR (rhPCR): improved specificity and single nucleotide polymorphism detection using blocked cleavable primers, BMC Biotechnol, 11:80. Exemplary enzymes that can be used to practice methods as provided herein include for example PHUSION HOT START II®, a commercially available thermostable DNA polymerase, one of many that are available and can be used to practice methods as provided herein, see for example, Ishino S, Ishino Y, DNA polymerases as useful reagents for biotechnology—the history of developmental research in the field, Front Microbiol. 2014 Aug. 29; 5:465). Exemplary conditions for In alternative embodiments, provided are methods comprising use of digital PCR, see for example Morley A A. Digital PCR: A brief history. Biomol Detect Quantif. 2014 Aug. 15; 1(1):1-2, or Digital PCR, or dPCR, including for example, Droplet Digital PCR (ddPCR), for use in methods as provided herein, for example, for the production of amplicons of interest, or for producing new extended DNA polynucleotides; and methods as provided herein can be practiced using any method known in the art, for example as described by U.S. Pat. No. 9,797,007.

Synthetic Nucleic Acids

In alternative embodiments, provided are synthetic DNA polynucleotides comprising at least a single ribonucleotide residue (referred to as a selector nucleotide) that can be located at the first (ultimate), second (penultimate), third (antepenultimate), fourth (preantepenultimate), fifth (propreantepenultimate), or sixth (one before the propreantepenultimate) position in reference to a 3' end of the synthetic DNA polynucleotide (or selector nucleotide), and in alternative embodiments, a second or third or additional ribonucleotide residues are included in the provided in the synthetic DNA polynucleotide.

In alternative embodiments, selector polynucleotides are used as primers in amplification methods capable of selecting against amplification of a particular allele while not interfering with the amplification or retrieval of any alternative alleles or mutations at a particular nucleotide position within a target sequence. The design, composition, and manufacture of the selector polynucleotide is based on the allele that is to be suppressed. By way of example, if one is interested in single nucleotide mutations occurring at c.38 in the human oncogene KRAS, a chimeric DNA/RNA polynucleotide that is a perfect match to the wild type sequence and that contains a single ribonucleotide at the position corresponding to the site of interest would be created. Referring to FIG. 1, all of the sequences shown are identical to the wild type sequence, including the nucleotides in red and underlined in each sequence (this is the selector nucleotide and is the sole ribonucleotide in the sequence). The selector nucleotide can be at any of the positions depicted in FIG. 1, though the ultimate position is not preferred, and positions even more distal to the 3' end may at times also work as selector nucleotides. Referring to FIG. 3, the selector polynucleotide may be of a variety of lengths, including, but not limited to, the ones depicted. FIG. 9 displays results obtained using the selector polynucleotides listed in FIG. 1. In the presence of the thermostable RNase H2, all of the selector polynucleotides are effective in suppressing or partially suppressing the amplification of the wild type "G" containing sequence at position 38 (marked by arrows) while not interfering with the mutant "A" signal (in this case).

As described in Examples, the design, composition, and manufacture of selector polynucleotides for the suppression of wild type sequences without interfering with the detection of other alternatives, including, but not limited to, deletions, insertions, and in the case of cDNA, fusions, may also be accomplished. Since suppression is based on the sequence of the allele to be suppressed, alternative designs can be accomplished by one skilled in the art.

Sequencing Nucleic Acids

In alternative embodiments, provided are methods wherein the sequence of an amplicon, or a new extended DNA polynucleotide, is determined by DNA sequencing, optionally using a method comprising use of Sanger sequencing, or next generation sequencing (NGS), single molecule real time (SMRT) sequencing, nanopore DNA sequencing, reversible terminated chemistry (for example, SOLEXA technology (Illumina)), combinatorial probe anchor synthesis (cPAS), mass spectrometry sequencing, or massively parallel signature sequencing (MPSS) or any equivalent thereof or any combination thereof.

Any sequencing method known in the art can be used to sequence an amplicon, or a new extended DNA polynucleotide, produced by a method as provided herein.

Products of Manufacture and Kits

Provided are products of manufacture and kits for practicing methods as provided herein; and optionally, products of manufacture and kits can further comprise instructions for practicing methods as provided herein.

Any of the above aspects and embodiments can be combined with any other aspect or embodiment as disclosed here in the Summary, Figures and/or Detailed Description sections.

As used in this specification and the claims, the singular forms "a," "an" and "the" include plural referents unless the context clearly dictates otherwise.

Unless specifically stated or obvious from context, as used herein, the term "or" is understood to be inclusive and covers both "or" and "and".

Unless specifically stated or obvious from context, as used herein, the term "about" is understood as within a range of normal tolerance in the art, for example within 2 standard deviations of the mean. About can be understood as within 20%, 19%, 18%, 17%, 16%, 15%, 14%, 13%, 12% 11%, 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Unless specifically stated or obvious from context, as used herein, the terms "substantially all", "substantially most of", "substantially all of" or "majority of" encompass at least about 90%, 95%, 97%, 98%, 99% or 99.5%, or more of a referenced amount of a composition.

The entirety of each patent, patent application, publication and document referenced herein hereby is incorporated by reference. Citation of the above patents, patent applications, publications and documents is not an admission that any of the foregoing is pertinent prior art, nor does it constitute any admission as to the contents or date of these publications or documents. Incorporation by reference of these documents, standing alone, should not be construed as an assertion or admission that any portion of the contents of any document is considered to be essential material for satisfying any national or regional statutory disclosure requirement for patent applications. Notwithstanding, the right is reserved for relying upon any of such documents, where appropriate, for providing material deemed essential to the claimed subject matter by an examining authority or court.

Modifications may be made to the foregoing without departing from the basic aspects of the invention. Although the invention has been described in substantial detail with reference to one or more specific embodiments, those of ordinary skill in the art will recognize that changes may be made to the embodiments specifically disclosed in this application, and yet these modifications and improvements are within the scope and spirit of the invention. The invention illustratively described herein suitably may be practiced in the absence of any element(s) not specifically disclosed herein. Thus, for example, in each instance herein any of the terms "comprising", "consisting essentially of", and "consisting of" may be replaced with either of the other two terms. Thus, the terms and expressions which have been employed are used as terms of description and not of limitation, equivalents of the features shown and described, or portions thereof, are not excluded, and it is recognized that various modifications are possible within the scope of the invention. Embodiments of the invention are set forth in the following claims.

The invention will be further described with reference to the examples described herein; however, it is to be understood that the invention is not limited to such examples.

EXAMPLES

Unless stated otherwise in the Examples, all recombinant DNA techniques are carried out according to standard protocols, for example, as described in Sambrook et al. (2012) Molecular Cloning: A Laboratory Manual, 4th Edition, Cold Spring Harbor Laboratory Press, NY and in Volumes 1 and 2 of Ausubel et al. (1994) Current Protocols in Molecular Biology, Current Protocols, USA. Other references for standard molecular biology techniques include Sambrook and Russell (2001) Molecular Cloning: A Laboratory Manual, Third Edition, Cold Spring Harbor Laboratory Press, NY, Volumes I and II of Brown (1998) Molecular Biology LabFax, Second Edition, Academic Press (UK). Standard materials and methods for polymerase chain reactions can be found in Dieffenbach and Dveksler (1995) PCR Primer: A Laboratory Manual, Cold Spring Harbor Laboratory Press, and in McPherson at al. (2000) PCR—Basics: From Background to Bench, First Edition, Springer Verlag, Germany.

In alternative embodiments, the differences noted in the Examples is detected by sequencing, hybridization, mass spectrometry, or any other technology that can detect sequence changes, including those with nucleotide resolution.

Example 1: Suppression of One Allele while Simultaneously Amplifying any Alternative Allele This example describes and demonstrates the efficacy of exemplary methods as provided herein for selectively suppressing one allele while simultaneously amplifying any alternative allele. This example also describes and demonstrates the efficacy of exemplary methods for suppressing a wild type sequence while simultaneously amplifying a point mutation.

In alternative embodiments, exemplary methods as provided herein comprise suppressing the exponential amplification of KRAS DNA that codes for the wild type "G" nucleotide at coding position 35 (in this example, KRAS c.35) while simultaneously allowing exponential amplification of any of the three mutations possible at this position. Mutations at this position are the most frequent cancer-causing KRAS mutations representing approximately 65% of the point mutations in KRAS codons 12 and 13. The selector primer used would contain a "G" ribonucleotide (riboG or rG) at the antepenultimate position, be a perfect match to the wild type template, and be extended by the proofreading DNA polymerase enzyme. Since the newly formed duplex DNA retains the riboG, thermostable ribonuclease H2 (TS RNase H2), present in the reaction, cuts at the 5' side of the ribonucleotide and detaches most of the primer sequence; exponential amplification is suppressed. In contrast, templates that code for the c.35G>A (p.G12D) mutation; or c.35G>T (p.G12V) mutation; or c.35G>C (p.G12A) mutation are not a match for the selector primer at the antepenultimate position, resulting in the 3' to 5' exonuclease activity of the proofreading polymerase digesting the primer back through the mismatch and the ribonucleotide is eliminated prior to extension of the primer over the mutant site. The loss of the ribonucleotide makes the incorporated primer sequence resistant to removal by ribonuclease. The return primer copies over the incorporated (i.e., partially digested, then extended) first primer and any mutant sequence is exponentially amplified.

Non-limiting examples of a proofreading DNA polymerase that can be used in methods as provided herein include PHUSION HOT START II DNA Polymerase (ThermoFisher Scientific, cat. #F549L); Q5 HOT START HIGH-FIDELITY® DNA Polymerase (New England Biolabs, cat. #M0493L); and PLATINUM SUPERFI II® DNA Polymerase (ThermoFisher Scientific, cat. #12361050).

A non-limiting example of a thermostable ribonuclease H2 that can be used in methods as provided herein is RNase H2 enzyme (IDT, cat. #Nov. 3, 2002-03).

This exemplary method includes distinct advantages over current methods, including never introducing primers that contain the sequence that one is interested in detecting; a mutant is only detected if: 1. The mismatch between selector primer and mutated template is recognized and removed by the 3' to 5' exonuclease activity of the proofreading polymerase, and 2. If the high-fidelity polymerase copies over the mutated template. In contrast, allele-specific amplification introduces the variant sequence that one is interested in detecting, which can lead to false positives. Another advantage is that a single primer detects any variant at a particular nucleotide position; in contrast, allele-specific PCR needs a specific primer for each allele variant or mutation.

Example 2: Suppression of a Wild Type Sequence while Simultaneously Amplifying a DNA Deletion This example demonstrates exemplary methods for suppressing the amplification of a wild type DNA while simultaneously amplifying a template that contains a deletion.

In alternative embodiments, exemplary methods as provided herein comprise suppressing the exponential amplification of wild type epidermal growth factor receptor (EGFR) DNA while simultaneously allowing exponential amplification of DNA with the inframe deletion, c.2235_2249del (p.E746_A750del). Inframe deletions represent approximately 41% of all EGFR mutations in cancer, and this particular mutation is among the more frequent ones.

The 3' end of the selector primer ends with GAA, contains a "G" ribonucleotide (riboG or rG) at the antepenultimate position, and is a perfect match for the wild type EGFR codon that codes for the glutamic acid residue at amino acid position 746. Since the newly formed duplex DNA retains the riboG, thermostable ribonuclease H2 (TS RNase H2), present in the reaction, cuts at the 5' side of the ribonucleotide and detaches most of the primer sequence, resulting in having exponential amplification suppressed.

In contrast, templates for the c.2235_2249del (p.E746_A750del) deletion are not a match for the selector primer at the antepenultimate position, resulting in the 3' to 5' exonuclease activity of the proofreading polymerase digesting the primer back through the mismatch and the ribonucleotide is eliminated prior to extension of the primer over the mutant site. The loss of the ribonucleotide makes the incorporated primer sequence resistant to removal by ribonuclease. The return primer copies over the incorporated (i.e., partially digested, then extended) first primer and any mutant sequence is exponentially amplified.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® HOT START HIGH-FIDELITY® DNA Polymerase (New England Biolabs, cat. #M0493L); and PLATINUM SUPERFI II® DNA Polymerase (ThermoFisher Scientific, cat. #12361050). A non-limiting example of a thermostable ribonuclease H2 that can be used to practice methods as provided herein is RNase H2 enzyme (IDT, cat. #Nov. 3, 2002-03).

This exemplary method includes distinct advantages over current methods, including never introducing primers that contain the sequence that one is interested in detecting; in contrast, allele-specific amplification introduces the variant sequence that one is interested in detecting, which can lead to false positives. Another advantage is that a single primer detects any variant at a particular nucleotide position; in contrast, allele-specific PCR needs a specific primer for each allele variant or mutation.

Example 3: Suppression of a Wild Type Sequence while Simultaneously Amplifying a DNA Insertion This example demonstrates exemplary methods for suppressing the amplification of a wild type DNA while simultaneously amplifying a template that contains an insertion.

A non-limiting example would be suppressing the exponential amplification of wild type EGFR DNA while simultaneously allowing exponential amplification of DNA with the c.2300_2308dup (p.A767_V769dup) insertion. This insertion is a duplication, and patients with it often have decreased sensitivity to first- and second-generation EGFR tyrosine kinase inhibitors (TKIs). The 3' end of the selector primer ends with ACA, contains an "A" ribonucleotide (riboA or rA) at the antepenultimate position, and is a perfect match for the wild type EGFR codon that codes for the aspartic acid residue at amino acid position 770. Since the newly formed duplex DNA retains the riboA, thermostable ribonuclease H2 (TS RNase H2), present in the reaction, cuts at the 5' side of the ribonucleotide and detaches most of the primer sequence; exponential amplification is suppressed. In contrast, templates containing the c.2300_2308dup (p.A767_V769dup) insertion are not a match for the selector primer at the antepenultimate position, resulting in the 3' to 5' exonuclease activity of the proofreading polymerase digesting the primer back through the mismatch and the ribonucleotide is eliminated prior to extension of the primer over the mutant site. The loss of the ribonucleotide makes the incorporated primer sequence resistant to removal by ribonuclease. The return primer copies over the incorporated (i.e., partially digested, then extended) first primer and any mutant sequence is exponentially amplified.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® HOT START HIGH-FIDELITY® DNA Polymerase (New England Biolabs, cat. #M0493L); and PLATINUM SUPERFI II® DNA Polymerase (ThermoFisher Scientific, cat. #12361050).

A non-limiting example of a thermostable ribonuclease H2 that can be used to practice methods as provided herein is RNase H2 enzyme (IDT, cat. #Nov. 3, 2002-03).

This exemplary method includes distinct advantages over current methods, including never introducing primers that contain the sequence that one is interested in detecting; in contrast, allele-specific amplification introduces the variant sequence that one is interested in detecting, which can lead to false positives. Another advantage is that a single primer detects any variant at a particular nucleotide position; in contrast, allele-specific PCR needs a specific primer for each allele variant or mutation.

Example 4: Suppression of a Wild Type cDNA Sequence while Simultaneously Amplifying a cDNA Coding for a Fusion Protein This example demonstrates exemplary methods for suppressing the amplification of a wild type cDNA while simultaneously amplifying a template that codes for a fusion protein.

A non-limiting example would be suppressing the exponential amplification of wild type echinoderm microtubule-associated protein-like 4 (EML4) while simultaneously allowing exponential amplification of a cDNA that codes for an EML4-ALK fusion protein (ALK stands for Anaplastic lymphoma kinase, also known as ALK tyrosine kinase receptor or CD246). EML4-ALK fusion protein has been found in non-small cell lung cancer (NSCLC) and is the target for Crizotinib, among other targeted therapies. A cDNA preparation is first made, followed by amplification using a selector primer with the sequence GTG at its 3' end, where the antepenultimate "G" is a ribonucleotide (riboG or rG) and is a perfect match for the wild type EML4 sequence.

Since the newly formed duplex DNA retains the riboG, thermostable ribonuclease H2 (TS RNase H2), present in the reaction, cuts at the 5' side of the ribonucleotide and detaches most of the primer sequence; exponential amplification is suppressed. In contrast, EML4-ALK fusion templates are not a match for the selector primer at the antepenultimate position, resulting in the 3' to 5' exonuclease activity of the proofreading polymerase digesting the primer back through the mismatch and the ribonucleotide is eliminated prior to extension of the primer over the mutant site. The loss of the ribonucleotide makes the incorporated primer sequence resistant to removal by ribonuclease. The return primer copies over the incorporated (i.e., partially digested, then extended) first primer and any mutant sequence is exponentially amplified.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® START HIGH-FIDELITY® DNA Polymerase (New England Biolabs, cat. #M0493L); and PLATINUM SUPERFI II® DNA Polymerase (ThermoFisher Scientific, cat. #12361050).

A non-limiting example of a thermostable ribonuclease H2 that can be used to practice methods as provided herein is RNase H2 enzyme (IDT, cat. #Nov. 3, 2002-03). A non-limiting example of a reverse transcriptase used to make the cDNA from an mRNA template that can be used to practice methods as provided herein is SUPERSCRIPT™ III Reverse Transcriptase (ThermoFisher Scientific, cat. #18080085).

This exemplary method includes distinct advantages over current methods, including never introducing primers that contain the sequence that one is interested in detecting; in contrast, allele-specific amplification introduces the variant sequence that one is interested in detecting, which can lead to false positives.

Example 5: Suppression of One Allele while Simultaneously Amplifying any Alternative Allele: Application to Determining Modified or Unmodified Nucleotide Status This example demonstrates exemplary methods for suppressing the amplification of one allele while simultaneously amplifying any alternative allele present at the nucleotide position, specifically, when one or the other allele has been created based on the presence or absence of a nucleotide modification. A non-limiting example would be when an unmodified cytosine nucleotide is changed into a deoxyuridine (dU) while a methylated or hydroxymethylated cytosine is not.

A non-limiting example would be use of a selector primer that contains a "G" ribonucleotide (riboG or rG) at the antepenultimate position, is a perfect match to the treated template (which in the complementary position remains a "C" since it is modified and therefore not changed), and is extended by a proofreading enzyme. Since the newly formed duplex DNA retains the riboG, thermostable ribonuclease H2 (TS RNase H2), present in the reaction, cuts at the 5' side of the ribonucleotide and detaches most of the primer sequence; exponential amplification is suppressed. In contrast, in treated templates where the "C" has been changed to "dU" there is not a match for the selector primer at the antepenultimate position, resulting in the 3' to 5' exonuclease activity of the proofreading polymerase digesting the primer back through the mismatch and the ribonucleotide is eliminated prior to extension of the primer over the "dU" site (pairing an "A" with it). The loss of the ribonucleotide makes the incorporated primer sequence resistant to removal by ribonuclease. The return primer copies over the incorporated (i.e., partially digested, then extended) first primer and the "dU" sequence is exponentially amplified (being changed to a "T" during amplification).

A non-limiting example would be the converse of the aforementioned, where the selector primer now contains an "A" ribonucleotide (riboA or rA) at the antepenultimate position, is a perfect match to the treated template (which in the complementary position becomes a "dU" since it was unmodified and therefore changed), and is extended by a proofreading enzyme. Since the newly formed duplex DNA retains the riboA, thermostable ribonuclease H2 (TS RNase H2), present in the reaction, cuts at the 5' side of the ribonucleotide and detaches most of the primer sequence; exponential amplification is suppressed. In contrast, in treated templates where the "C" has not been changed (protected by the modification) there is not a match for the selector primer at the antepenultimate position, resulting in the 3' to 5' exonuclease activity of the proofreading polymerase digesting the primer back through the mismatch and the ribonucleotide is eliminated prior to extension of the primer over the mutant site. The loss of the ribonucleotide makes the incorporated primer sequence resistant to removal by ribonuclease. The return primer copies over the incorporated (i.e., partially digested, then extended) first primer and the sequence is exponentially amplified.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® HOT START HIGH-FIDELITY® DNA Polymerase (New England Biolabs, cat. #M0493L); and PLATINUM SUPERFI II® DNA Polymerase (ThermoFisher Scientific, cat. #12361050).

This exemplary method includes distinct advantages over current methods, including never introducing primers that contain the sequence that one is interested in detecting; in contrast, allele-specific amplification introduces the variant sequence that one is interested in detecting, which can lead to false positives.

Example 6: Suppression of One Allele while Simultaneously Amplifying any Alternative Allele: Application to Molecular Haplotyping This example demonstrates exemplary methods for suppressing the amplification of one allele while simultaneously amplifying any alternative allele present at the nucleotide position along with alleles located on the same DNA homologue as the alternative allele thus allowing molecular haplotyping.

A non-limiting example would be determining the presence or absence of the AGT haplotype in the ITGA4 gene. Single nucleotide polymorphisms within the ITGA4 gene include c.1845G>A, c.2633A>G, and c.2883C>T and the haplotype AGT is associated with the development of antibody-mediated rejection in heart transplant patients. If genotyping reveals an individual is heterozygous at two or three of the sites, then haplotypes can be determined using a selector primer to an appropriate heterozygous site and a return primer located beyond the most distal heterozygous site. By way of example, if a DNA is heterozygous at c. 1845, then the selector primer would contain a "G" ribonucleotide (riboG or rG) at the antepenultimate position, corresponding to the c. 1845 position; the return primer would be downstream of the c.2883 position. This would lead to the suppression of the c. 1845G allele while allowing exponential amplification of the c. 1845A allele. Because of the high fidelity and the very low level of strand-switching of the proofreading enzyme used, alleles present on the same DNA homologue that is exponentially amplified can be determined and the haplotype found for the 1845A DNA homologue. The haplotype for the other homologue can be inferred from the genotype or confirmed in a separate reaction using a selector primer containing an "A" ribonucleotide (riboA or rA) at the antepenultimate position.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® HOT START HIGH-FIDELITY® DNA Polymerase (New England Biolabs, cat. #M0493L); and PLATINUM SUPERFI II® DNA Polymerase (ThermoFisher Scientific, cat. #12361050).

A non-limiting example of a thermostable ribonuclease H2 that can be used to practice methods as provided herein is RNase H2 enzyme (IDT, cat. #Nov. 3, 2002-03).

This exemplary method includes distinct advantages over current methods, including never introducing primers that contain the sequence that one is interested in detecting; in contrast, allele-specific amplification introduces the variant sequence that one is interested in detecting, which can lead to false positives. Another advantage is that a single primer detects any variant at a particular nucleotide position; in contrast, allele-specific PCR needs a specific primer for each allele variant or mutation.

Example 7: Partial Suppression of One Allele while Simultaneously Amplifying any Alternative Allele This example demonstrates exemplary methods for partially suppressing the amplification of one allele while simultaneously amplifying any alternative allele present at the nucleotide position. This can also be applied to the partial suppression of a wild type sequence while simultaneously amplifying a point mutation. Referring to the latter case, by only partially suppressing the amplification of the wild type while not interfering with the amplification of any mutant, two outcomes can be accomplished: 1. If no mutant is present, then the partial amplification of the wild type provides an internal control that confirms that the overall reaction worked; and 2. By controlling the level of suppression of the wild type an internal standard is provided to which the level of amplification of the mutant (if present) can be compared.

A non-limiting example would be partially suppressing the exponential amplification of KRAS DNA that codes for the wild type "G" nucleotide at coding position 35 while simultaneously allowing exponential amplification of any of the three mutations possible at this position. The selector primer would contain a "G" ribonucleotide (riboG or rG) at the antepenultimate position, be a perfect match to the wild type template, and be extended by the proofreading enzyme. Mixed in with the selector primer at a predetermined amount would be a counterpart that is identical to the selector primer except the "G" at the antepenultimate position would not be a ribonucleotide, but a normal deoxyribonucleotide. Newly formed duplex DNA that retains the riboG would be cut by thermostable ribonuclease H2 (TS RNase H2) present in the reaction, which detaches most of the primer sequence; exponential amplification is suppressed. However, newly formed duplex DNA that contains the counterpart to the selector primer (i.e., primer containing the normal deoxynucleotide counterpart at the selector nucleotide position) would not be cut and the entirety of the primer retained. Exponential amplification of the wild type would be only partially suppressed. Templates that code for the c.35G>A (p.G12D) mutation; or c.35G>T (p.G12V) mutation; or c.35G>C (p.G12A) mutation are not a match for the selector primer (or its counterpart) at the antepenultimate position, resulting in the 3' to 5' exonuclease activity of the proofreading polymerase digesting the primer back through the mismatch and the ribonucleotide or its deoxyribonucleotide counterpart is eliminated prior to extension of the primer over the mutant site. The absence of any ribonucleotide makes the incorporated primer sequence resistant to removal by ribonuclease. The return primer copies over the incorporated (i.e., partially digested, then extended) first primer and any mutant sequence is exponentially amplified.

Non-limiting examples of a proofreading polymerase that can be used to practice methods as provided herein includes PHUSION HOT START II® DNA Polymerase (ThermoFisher Scientific, cat. #F549L); Q5 HOT START HIGH-FIDELITY® HOT START HIGH-FIDELITY® DNA Polymerase (New England Biolabs, cat. #M0493L); and PLATINUM SUPERFI II® DNA Polymerase (ThermoFisher Scientific, cat. #12361050).

A non-limiting example of a thermostable ribonuclease H2 that can be used to practice methods as provided herein is RNase H2 enzyme (IDT, cat. #Nov. 3, 2002-03).

This exemplary method includes distinct advantages over current methods, including never introducing primers that contain the sequence that one is interested in detecting; a mutant is only detected if: 1. The mismatch between selector primer and mutated template is recognized and removed by the 3' to 5' exonuclease activity of the proofreading polymerase, and 2. If the high-fidelity polymerase copies over the mutated template. In contrast, allele-specific amplification introduces the variant sequence that one is interested in detecting, which can lead to false positives. Another advantage is that a single primer detects any variant at a particular nucleotide position; in contrast, allele-specific PCR needs a specific primer for each allele variant or mutation. Another advantage as described in this Example and applicable to the other Examples, and generally to all methods as provided herein, is the ability to allow a set amount of amplification of a particular allele or wild type that serves as an internal control demonstrating that the reaction has worked; and as an internal standard to which the level of amplification of the alternative allele or mutant can be compared (if present).

A number of embodiments of the invention have been described. Nevertheless, it can be understood that various modifications may be made without departing from the spirit and scope of the invention. Accordingly, other embodiments are within the scope of the following claims.

What is claimed is:

1. A method for amplifying nucleic acid for differentiating a first nucleic acid sequence from a second nucleic acid sequence wherein the first and the second nucleic acid are in the same amplification reaction mixture, comprising:

(a) providing or having provided a selector polynucleotide, wherein the selector polynucleotide contains therein a selector nucleotide residue, wherein the selector polynucleotide comprises at least a single residue selector nucleotide that is located at the first (ultimate), second (penultimate), third (antepenultimate), fourth (preantepenultimate), fifth (propreantepenultimate), or sixth (one residue to the 5' side of the propreantepenultimate) position in reference to a 3' end, or is at a position that is even more distal to the 3' end, wherein the at least single residue selector nucleotide is structurally dissimilar to all other nucleotide residues within the region of the selector polynucleotide needed for annealing or hybridizing of the selector polynucleotide to a target nucleic acid, and the selector polynucleotide has a 3' end that can be: extended by a DNA polymerase, or processed to have a 3' end that can be extended by a DNA polymerase;

(b) providing or having provided a DNA polynucleotide or plurality of DNA polynucleotides;

(c) contacting, annealing or hybridizing, the selector polynucleotide to the DNA polynucleotide or plurality of DNA polynucleotides, wherein the DNA polynucleotide or plurality of DNA polynucleotides acts as a template DNA polynucleotide to the selector polynucleotide under conditions wherein the selector polynucleotide anneals or specifically hybridizes to a complementary sequence or substantially complementary sequence in the DNA polynucleotide or plurality of DNA polynucleotides, thereby generating a nucleic acid duplex;

wherein the selector polynucleotide is either matched to the template DNA polynucleotide at the position of the selector nucleotide residue or is not matched to the template DNA polynucleotide at the position of the selector nucleotide residue;

(d) contacting the nucleic acid duplex with a DNA polymerase enzyme having 5' to 3' extension activity and having a 3' to 5' exonuclease activity, and/or a DNA polymerase enzyme having 5' to 3' extension activity and an enzyme having 3' to 5' exonuclease activity, under conditions wherein the DNA polymerase enzyme and/or the polymerase enzyme having 5' to 3' extension activity and the enzyme having 3' to 5' exonuclease activity are enzymatically active, wherein either:

(i) the selector nucleotide residue is mismatched between the selector polynucleotide and the DNA polynucleotide or plurality of DNA polynucleotides, and the 3' to 5' exonuclease activity results in enzymatically removing portions of the selector polynucleotide from the 3' end including the selector nucleotide residue and all nucleotides 3' of the selector nucleotide prior to the DNA polymerase enzymatically extending what remains of the selector polynucleotide to generate a new extended DNA polynucleotide that does not retain the selector nucleotide residue); or (ii) the DNA polymerase enzymatically extends a selector polynucleotide that is matched at the selector nucleotide residue with the DNA polynucleotide or plurality of DNA polynucleotides, without removing the selector nucleotide, thus retaining or incorporating the selector nucleotide residue of the selector polynucleotide into a new extended DNA polynucleotide; and (e) contacting the nucleic acid duplex with a ribonuclease enzyme, wherein:

(i) if the selector nucleotide residue has been removed by the 3' to 5' exonuclease activity, then the portion of the selector polynucleotide that was 5' to the single selector nucleotide is retained within the new extended synthetic polynucleotide; or (ii) if the selector nucleotide residue is retained in the extended selector polynucleotide and is matched to a deoxyribonucleotide residue, then the ribonuclease enzyme cuts at the selector nucleotide residue thereby detaching the portion of the new extended polynucleotide that was 5' to the selector nucleotide residue, wherein a new extended polynucleotide that retains the portion of the selector polynucleotide that had been 5' to the selector nucleotide residue is exponentially amplified, and wherein a new extended polynucleotide that has had the portion of the selector polynucleotide that was 5' to the selector nucleotide residue detached from the extended polynucleotide cannot be exponentially amplified and amplification is thereby selectively suppressed, thereby differentiating the first nucleic acid sequence from the second nucleic acid sequence.

2. The method of claim 1, wherein the enzyme used to cut on the 5' side of the single selector ribonucleotide is a ribonuclease H2.

3. A method for diagnosing a disease or a condition comprising determining if an individual in need thereof has the disease or condition by determining the presence or absence of an allele or a genomic sequence associated with or diagnostic of the disease or condition, wherein the presence or absence of the allele or genomic sequence associated with or diagnostic of the disease or condition is determined by using a method of claim 1.

4. The method of claim 3, wherein the disease is a cancer.

5. A method for treating, ameliorating or preventing a disease or a condition comprising treating an individual in need thereof with a drug, drug combination or treatment regimen indicated for the disease or condition, wherein the individual in need thereof is diagnosed as having, or predisposed to having, the disease or condition using a diagnostic method of claim 3.

6. The method for detecting the presence or absence of an allele in a biological specimen, comprising using a method of claim 1.

7. The method of claim 6, wherein detecting the presence or absence of the allele in the biological specimen is for: detection of cancer, non-invasive pre-natal testing (NIPT), to assess tissue compatibility or detecting donor-derived nucleic acid following organ transplant, to assess anti-microbial resistance (AMR) or early detection of microbial resistance in the individual in need thereof, or assessing the presence of minimum residual disease (MRD).

8. The method of claim 1, wherein the method further comprises a second selector polynucleotide or primer, that is identical to a first selector polynucleotide, except that the selector nucleotide residue is replaced by a corresponding normal deoxyribonucleotide to create a DNA amplification primer, and specific amounts of this DNA amplification primer are mixed with the first selector polynucleotide, or primer, containing a selector nucleotide residue in order to allow a certain amount of new extended DNA polynucleotide to be produced that would otherwise contain the selector nucleotide residue, but now lacks the selector nucleotide residue and is thereby now resistant to cutting by reagents or enzymes specific to the selector nucleotide, wherein the new extended DNA polynucleotide so produced by the second selector polynucleotide is used as internal reaction controls to demonstrate that the amplification worked and as internal standards to which amounts of new extended DNA polynucleotides, produced by the first selector polynucleotide can be compared.

9. The method of claim 1, wherein the sequence of the new extended DNA polynucleotide, is determined by DNA sequencing.

10. The method of claim 1, wherein the identity of the nucleotide corresponding to the position of an original selector nucleotide residue is determined by extension of a primer over the site of interest.

11. The method of claim 1, wherein the production of the new extended DNA polynucleotide is determined or quantified by quantitative PCR (qPCR) or digital PCR.

12. The method of claim 1, wherein:

(a) the DNA polynucleotide or plurality of DNA polynucleotides are derived from a cell genome, a microbial genome or a viral genome:

(b) the genome, cDNA, cDNA library or genomic library is derived from a eukaryote or a prokaryote, a plant, an animal, or a mammal;

(c) the genome, cDNA, cDNA library or genomic library is derived from a human, (d) the genome, cDNA, cDNA library or genomic library is derived from a microorganism, (e) the genome, cDNA, cDNA library or genomic library is derived from a bacterium, an algae, a protist, an Archea or a fungus, or (f) the genome, cDNA, cDNA library or genomic library is derived from a virus or a bacteriophage.

13. The method of claim 1, wherein in the synthetic DNA polynucleotide:

(a) the single selector nucleotide residue is located at the second position from the 3' end, or the penultimate position of the selector polynucleotide;

(b) the single selector nucleotide residue is located at the third position from the 3' end, or the antepenultimate position of the or selector polynucleotide;

(c) the single selector nucleotide residue is located at the first position from the 3' end, or the ultimate position of the polynucleotide;

(d) the single selector nucleotide residue is located at the fourth position from the 3' end, or the preantepenultimate position of the selector polynucleotide;

(e) the single selector nucleotide residue is located at the fifth position from the 3' end, or the propreantepenultimate position of the selector polynucleotide;

(f) the single selector nucleotide residue is located at the sixth position from the 3' end, or one residue to the 5' side of the propreantepenultimate position of the polynucleotide;

(g) the selector nucleotide is a ribonucleotide, or the selector nucleotide comprises or is composed of at least one ribonucleotide; or (h) the selector nucleotide comprises or is composed of or at least one synthetic or non-natural nucleotide.

14. The method of claim 5, wherein the disease is a cancer, or the condition is an inherited disease or genetic condition.

15. The method of claim 1, wherein in step (b) the DNA polynucleotide or plurality of DNA polynucleotides comprise or is derived from a genome, a cDNA, a cDNA library or a genomic library.

16. The method of claim 1, wherein in step (e) the ribonuclease enzyme is thermostable.

17. The method of claim 16, wherein the thermostable ribonuclease is a thermostable ribonuclease H2 enzyme under conditions wherein the thermostable ribonuclease enzyme is active.

18. The method of claim 10, wherein:

(a) the identity and relative amounts of the nucleotides at the site of interest are determined by using or by means of a label or by mass, or (b) the identity and relative amounts of the nucleotides at the site of interest are determined by methods comprising single-base extension of a primer across the site of interest in the new extended DNA polynucleotide created using the selector polynucleotide.

19. The method of claim 9, wherein the sequence of the new extended DNA polynucleotide is determined by DNA sequencing.

20. The method of claim 19, wherein the sequence of the new extended DNA polynucleotide is determined by use of Sanger sequencing, next generation sequencing (NGS), single molecule real time (SMRT) sequencing, nanopore DNA sequencing, reversible terminated chemistry, combinatorial probe anchor synthesis (cPAS), mass spectrometry sequencing, or massively parallel signature sequencing (MPSS).

21. The method of claim 1, wherein:

(a) the method further comprises a second selector polynucleotide or primer, that is identical to a first selector polynucleotide, except that the selector nucleotide residue is replaced by a corresponding normal deoxyribonucleotide to create a DNA amplification primer, and specific amounts of this DNA amplification primer are mixed with the first selector polynucleotide, or primer, containing a selector nucleotide residue in order to allow a certain amount of a new extended polynucleotide to be produced that would otherwise contain the selector nucleotide residue, but now lacks the selector nucleotide residue and is thereby now resistant to cutting by reagents or enzymes specific to the selector nucleotide, wherein the new extended polynucleotide so produced by the second selector polynucleotide is used as internal reaction controls to demonstrate that the amplification worked and as internal standards to which amounts of new extended DNA polynucleotide produced by the first selector polynucleotide can be compared;

(b) the sequence of the new extended DNA polynucleotide, is determined by DNA sequencing, (c) the sequence of the new extended DNA polynucleotide is determined by a method comprising use of Sanger sequencing, next generation sequencing (NGS), single molecule real time (SMRT) sequencing, nanopore DNA sequencing, reversible terminated chemistry, combinatorial probe anchor synthesis (cPAS), mass spectrometry sequencing, or massively parallel signature sequencing (MPSS);

(d) the identity of the nucleotide corresponding to the position of an original selector nucleotide residue is determined by extension of a primer over the site of interest;

(e) the identity and relative amounts of the nucleotides at the site of interest are determined by using or by means of a label or by mass;

(f) the identity and relative amounts of the nucleotides at the site of interest are determined by methods comprising single-base extension of a primer across the site of interest in the new extended DNA polynucleotide created using the selector polynucleotide; and/or (g) the production of the new extended DNA polynucleotide is determined by quantitative PCR (qPCR), digital PCR.

* * * * *